(12) United States Patent
Felder et al.

(10) Patent No.: US 9,017,851 B2
(45) Date of Patent: *Apr. 28, 2015

(54) STERILE HOUSING FOR NON-STERILE MEDICAL DEVICE COMPONENT

(75) Inventors: Kevin D. Felder, Cincinnati, OH (US); Christopher B. Anderson, Oak Grove, MN (US); Frederick E. Shelton, IV, Hillsboro, OH (US); Michael J. Stokes, Cincinnati, OH (US); Sora Rhee, Cincinnati, OH (US); Timothy G. Dietz, Terrace Park, OH (US); William D. Dannaher, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 399 days.

This patent is subject to a terminal disclaimer.

(21) Appl. No.: 13/151,498

(22) Filed: Jun. 2, 2011

(65) Prior Publication Data

US 2012/0115007 A1 May 10, 2012

Related U.S. Application Data

(60) Provisional application No. 61/410,603, filed on Nov. 5, 2010, provisional application No. 61/487,846, filed on May 19, 2011.

(51) Int. Cl.
*H01M 2/26* (2006.01)
*A61B 17/32* (2006.01)
(Continued)

(52) U.S. Cl.
CPC ..... *A61B 18/1442* (2013.01); *A61B 17/320068* (2013.01); *A61B 2017/00398* (2013.01); *A61B 18/00* (2013.01); *A61B 2017/291* (2013.01);
(Continued)

(58) Field of Classification Search
None
See application file for complete search history.

(56) References Cited

U.S. PATENT DOCUMENTS

| 1,754,806 A | 4/1930 | Stevenson |
| 3,297,192 A | 1/1967 | Swett |

(Continued)

FOREIGN PATENT DOCUMENTS

| DE | 102008051866 | 10/2010 |
| DE | 102009013034 | 10/2010 |

(Continued)

OTHER PUBLICATIONS

U.S. Appl. No. 12/576,776, filed Oct. 9, 2009, Boudreaux et al.

(Continued)

*Primary Examiner* — Milton I Cano
*Assistant Examiner* — Carmen Lyles-Irving
(74) *Attorney, Agent, or Firm* — Frost Brown Todd LLC

(57) ABSTRACT

An apparatus for powering a medical device includes a battery pack, a connection feature on the battery pack, and a protective layer. In some versions the protective layer covers the battery pack and the connection feature to provide a fluid tight seal. In some versions, the connection feature comprises at least one electrode, which may pierce the protective layer to establish electrical communication with the medical device from within the protective layer such that a non-sterile battery pack could be used to deliver power to a sterile medical device without compromising sterility of the medical device. The protective layer may form a compartment. The at least one electrode may have a conical shape to facilitate piercing the protective layer.

19 Claims, 9 Drawing Sheets

(51) Int. Cl.
  *A61B 18/00* (2006.01)
  *A61B 18/14* (2006.01)
  *H02J 7/00* (2006.01)
  *A61B 18/04* (2006.01)
  *A61B 17/00* (2006.01)
  *A61B 17/29* (2006.01)
  *A61B 19/00* (2006.01)
  *A61B 17/064* (2006.01)
  *A61B 18/12* (2006.01)
  *H01M 2/10* (2006.01)
  *A61B 17/285* (2006.01)

(52) U.S. Cl.
  CPC .................. A61B 2017/2929 (2013.01); A61B 2018/00791 (2013.01); A61B 2017/2931 (2013.01); *A61B17/320092* (2013.01); A61B 2019/4873 (2013.01); A61B 2017/2933 (2013.01); A61B 17/064 (2013.01); *H02J 7/0045* (2013.01); A61B 18/1233 (2013.01); A61B 2017/00473 (2013.01); A61B 2017/293 (2013.01); *A61B 18/1445* (2013.01); A61B 2017/294 (2013.01); A61B 2019/4815 (2013.01); H02J 2/26 (2013.01); A61B 2018/00178 (2013.01); H01M 2/10 (2013.01); A61B 2019/4868 (2013.01); A61B 2018/1226 (2013.01); *A61B 18/14* (2013.01); A61B 2017/00734 (2013.01); A61B 17/285 (2013.01); A61B 19/38 (2013.01); A61B 2017/00084 (2013.01); A61B 2018/1455 (2013.01); *A61B 18/12* (2013.01); A61B 2017/00482 (2013.01); A61B 2018/00988 (2013.01); *A61B 17/00234* (2013.01); A61B 2018/1412 (2013.01); A61B 2017/0046 (2013.01); *A61B 18/04* (2013.01); A61B 2017/00477 (2013.01)

(56) References Cited

U.S. PATENT DOCUMENTS

| | | | |
|---|---|---|---|
| 3,419,198 A | 12/1968 | Pettersen | |
| 3,619,671 A | 11/1971 | Shoh | |
| 4,034,762 A | 7/1977 | Cosens et al. | |
| 4,057,220 A | 11/1977 | Kudlacek | |
| 4,535,773 A | 8/1985 | Yoon | |
| 4,641,076 A | 2/1987 | Linden et al. | |
| 4,662,068 A | 5/1987 | Polonsky | |
| 4,666,037 A | 5/1987 | Weissman | |
| 4,717,018 A | 1/1988 | Sacherer et al. | |
| 4,717,050 A | 1/1988 | Wright | |
| 4,721,097 A | 1/1988 | D'Amelio | |
| 4,768,969 A | 9/1988 | Bauer et al. | |
| 4,800,878 A | 1/1989 | Cartmell | |
| 4,844,259 A | 7/1989 | Glowczewskie, Jr. et al. | |
| 4,878,493 A | 11/1989 | Pasternak et al. | |
| 5,071,417 A | 12/1991 | Sinofsky | |
| 5,107,155 A | 4/1992 | Yamaguchi | |
| 5,144,771 A | 9/1992 | Miwa | |
| 5,149,598 A * | 9/1992 | Sunshine | 429/1 |
| 5,169,733 A | 12/1992 | Savovic et al. | |
| 5,176,677 A | 1/1993 | Wuchinich | |
| 5,246,109 A | 9/1993 | Markle et al. | |
| 5,273,177 A | 12/1993 | Campbell | |
| 5,277,694 A | 1/1994 | Leysieffer et al. | |
| 5,308,358 A | 5/1994 | Bond et al. | |
| 5,322,055 A | 6/1994 | Davison | |
| 5,339,799 A | 8/1994 | Kami et al. | |
| 5,358,508 A | 10/1994 | Cobb et al. | |
| 5,361,902 A | 11/1994 | Abidin et al. | |
| 5,429,229 A | 7/1995 | Chester et al. | |
| 5,449,370 A | 9/1995 | Vaitekunas | |
| 5,454,378 A | 10/1995 | Palmer et al. | |
| 5,501,607 A | 3/1996 | Yoshioka et al. | |
| 5,507,297 A | 4/1996 | Slater et al. | |
| 5,561,881 A | 10/1996 | Klinger et al. | |
| 5,578,052 A | 11/1996 | Koros et al. | |
| 5,580,258 A | 12/1996 | Wakata | |
| 5,582,617 A | 12/1996 | Klieman et al. | |
| 5,590,778 A | 1/1997 | Dutchik | |
| 5,592,065 A | 1/1997 | Oglesbee et al. | |
| 5,597,531 A | 1/1997 | Liberti et al. | |
| 5,599,350 A | 2/1997 | Schulze et al. | |
| 5,630,420 A | 5/1997 | Vaitekunas | |
| 5,630,456 A | 5/1997 | Hugo et al. | |
| 5,690,222 A | 11/1997 | Peters | |
| 5,741,305 A | 4/1998 | Vincent et al. | |
| 5,776,155 A | 7/1998 | Beaupre et al. | |
| 5,800,336 A | 9/1998 | Ball et al. | |
| 5,817,128 A | 10/1998 | Storz | |
| 5,868,244 A | 2/1999 | Ivanov et al. | |
| 5,873,873 A | 2/1999 | Smith et al. | |
| 5,882,310 A | 3/1999 | Marian, Jr. | |
| 5,935,144 A | 8/1999 | Estabrook | |
| 5,938,633 A | 8/1999 | Beupre | |
| 5,944,737 A | 8/1999 | Tsonton et al. | |
| 5,951,575 A | 9/1999 | Bolduc et al. | |
| 5,980,510 A | 11/1999 | Tsonton et al. | |
| 5,997,531 A | 12/1999 | Loeb et al. | |
| 6,018,227 A | 1/2000 | Kumar et al. | |
| 6,051,010 A | 4/2000 | Dimatteo et al. | |
| 6,056,735 A | 5/2000 | Okada et al. | |
| 6,063,098 A | 5/2000 | Houser et al. | |
| 6,066,151 A | 5/2000 | Miyawaki et al. | |
| 6,083,191 A | 7/2000 | Rose | |
| 6,095,355 A * | 8/2000 | Jessen et al. | 215/247 |
| 6,099,537 A | 8/2000 | Sugai et al. | |
| 6,165,191 A | 12/2000 | Shibata et al. | |
| 6,204,592 B1 | 3/2001 | Hur | |
| 6,214,023 B1 | 4/2001 | Whipple et al. | |
| 6,246,896 B1 | 6/2001 | Dumoulin et al. | |
| 6,248,238 B1 | 6/2001 | Burtin et al. | |
| 6,325,811 B1 | 12/2001 | Messerly | |
| 6,339,368 B1 | 1/2002 | Leith | |
| 6,398,755 B1 | 6/2002 | Belef et al. | |
| 6,409,742 B1 | 6/2002 | Fulton, III et al. | |
| 6,500,176 B1 | 12/2002 | Truckai et al. | |
| 6,500,188 B2 | 12/2002 | Harper et al. | |
| 6,514,267 B2 | 2/2003 | Jewett | |
| 6,520,185 B1 | 2/2003 | Bommannan et al. | |
| 6,561,983 B2 | 5/2003 | Cronin et al. | |
| 6,609,414 B2 | 8/2003 | Mayer et al. | |
| 6,623,500 B1 | 9/2003 | Cook et al. | |
| 6,626,901 B1 | 9/2003 | Treat et al. | |
| 6,647,281 B2 | 11/2003 | Morency | |
| 6,650,975 B2 | 11/2003 | Ruffner | |
| 6,656,177 B2 | 12/2003 | Truckai et al. | |
| 6,658,301 B2 | 12/2003 | Loeb et al. | |
| 6,666,875 B1 | 12/2003 | Sakurai et al. | |
| 6,717,193 B2 | 4/2004 | Olewine et al. | |
| 6,730,042 B2 | 5/2004 | Fulton et al. | |
| 6,758,855 B2 | 7/2004 | Fulton, III et al. | |
| 6,761,698 B2 | 7/2004 | Shibata et al. | |
| 6,783,524 B2 | 8/2004 | Anderson et al. | |
| 6,815,206 B2 | 11/2004 | Lin et al. | |
| 6,821,671 B2 | 11/2004 | Hinton et al. | |
| 6,838,862 B2 | 1/2005 | Luu | |
| 6,860,880 B2 | 3/2005 | Treat et al. | |
| 6,869,435 B2 | 3/2005 | Blake | |
| 6,923,807 B2 | 8/2005 | Ryan et al. | |
| 6,982,696 B1 | 1/2006 | Shahoian | |
| 7,031,155 B2 | 4/2006 | Sauciuc et al. | |
| 7,077,853 B2 | 7/2006 | Kramer et al. | |
| 7,083,589 B2 | 8/2006 | Banko et al. | |
| 7,101,371 B2 | 9/2006 | Dycus et al. | |
| 7,112,201 B2 | 9/2006 | Truckai et al. | |
| 7,125,409 B2 | 10/2006 | Truckai et al. | |
| 7,150,712 B2 | 12/2006 | Buehlmann et al. | |
| 7,169,146 B2 | 1/2007 | Truckai et al. | |
| 7,186,253 B2 | 3/2007 | Truckai et al. | |
| 7,189,233 B2 | 3/2007 | Truckai et al. | |
| 7,220,951 B2 | 5/2007 | Truckai et al. | |

(56) References Cited

U.S. PATENT DOCUMENTS

| | | |
|---|---|---|
| 7,221,216 B2 | 5/2007 | Nguyen |
| 7,232,440 B2 | 6/2007 | Dumbauld et al. |
| 7,244,024 B2 | 7/2007 | Biscardi |
| 7,292,227 B2 | 11/2007 | Fukumoto et al. |
| 7,296,804 B2 | 11/2007 | Lechot et al. |
| 7,303,556 B2 | 12/2007 | Metzger |
| 7,309,849 B2 | 12/2007 | Truckai et al. |
| 7,311,709 B2 | 12/2007 | Truckai et al. |
| 7,349,741 B2 | 3/2008 | Maltan et al. |
| 7,354,440 B2 | 4/2008 | Truckal et al. |
| 7,364,554 B2 | 4/2008 | Bolze et al. |
| 7,381,209 B2 | 6/2008 | Truckai et al. |
| 7,416,101 B2 | 8/2008 | Shelton, IV et al. |
| 7,422,139 B2 | 9/2008 | Shelton, IV et al. |
| 7,464,846 B2 | 12/2008 | Shelton, IV et al. |
| 7,473,145 B2 | 1/2009 | Ehr et al. |
| 7,479,152 B2 | 1/2009 | Fulton, III et al. |
| 7,494,492 B2 | 2/2009 | Da Silva et al. |
| D594,983 S | 6/2009 | Price et al. |
| 7,563,142 B1 | 7/2009 | Wenger et al. |
| 7,583,564 B2 | 9/2009 | Kitahara et al. |
| 7,638,958 B2 | 12/2009 | Philipp et al. |
| 7,643,378 B2 | 1/2010 | Genosar |
| 7,717,312 B2 | 5/2010 | Beetel |
| 7,721,936 B2 | 5/2010 | Shalton, IV et al. |
| 7,738,971 B2 | 6/2010 | Swayze et al. |
| 7,766,910 B2 | 8/2010 | Hixson et al. |
| 7,766,929 B2 | 8/2010 | Masuda |
| 7,770,722 B2 | 8/2010 | Donahoe et al. |
| 7,776,037 B2 | 8/2010 | Odom |
| 7,780,660 B2 | 8/2010 | Bourne et al. |
| 7,815,658 B2 | 10/2010 | Murakami |
| 7,845,537 B2 | 12/2010 | Shelton, IV et al. |
| 7,846,155 B2 | 12/2010 | Houser et al. |
| 7,846,159 B2 | 12/2010 | Morrison et al. |
| 7,889,489 B2 | 2/2011 | Richardson et al. |
| 7,922,063 B2 | 4/2011 | Zemlok et al. |
| 7,948,208 B2 | 5/2011 | Partovi et al. |
| 7,952,322 B2 | 5/2011 | Partovi et al. |
| 7,952,873 B2 | 5/2011 | Glahn et al. |
| 7,959,050 B2 | 6/2011 | Smith et al. |
| 8,038,025 B2 | 10/2011 | Stark et al. |
| 8,040,107 B2 | 10/2011 | Ishii |
| 8,052,605 B2 | 11/2011 | Muller et al. |
| 8,058,771 B2 | 11/2011 | Giordano et al. |
| 8,075,530 B2 | 12/2011 | Taylor et al. |
| 8,097,011 B2 | 1/2012 | Sanai et al. |
| 8,142,461 B2 | 3/2012 | Houser et al. |
| 8,147,488 B2 | 4/2012 | Masuda |
| 8,177,776 B2 | 5/2012 | Humayun et al. |
| 8,195,271 B2 | 6/2012 | Rahn |
| 8,210,411 B2 | 7/2012 | Yates et al. |
| 8,216,212 B2 | 7/2012 | Grant et al. |
| 8,221,418 B2 | 7/2012 | Prakash et al. |
| 8,240,498 B2 | 8/2012 | Ramsey et al. |
| 8,246,642 B2 | 8/2012 | Houser et al. |
| 8,267,094 B2 | 9/2012 | Danek et al. |
| 8,277,446 B2 | 10/2012 | Heard |
| 8,292,888 B2 | 10/2012 | Whitman |
| 8,298,253 B2 | 10/2012 | Charles |
| 8,301,262 B2 | 10/2012 | Mi et al. |
| 8,336,725 B2 | 12/2012 | Ramsey et al. |
| 8,344,690 B2 | 1/2013 | Smith et al. |
| 8,377,059 B2 | 2/2013 | Deville et al. |
| 8,400,108 B2 | 3/2013 | Powell et al. |
| 8,425,545 B2 | 4/2013 | Smith et al. |
| 8,444,653 B2 | 5/2013 | Nycz et al. |
| 8,449,529 B2 | 5/2013 | Bek et al. |
| 8,487,487 B2 | 7/2013 | Dietz et al. |
| 8,564,242 B2 | 10/2013 | Hansford et al. |
| 8,617,077 B2 | 12/2013 | van Groningen et al. |
| 8,641,629 B2 | 2/2014 | Kurokawa |
| 8,663,112 B2 | 3/2014 | Slayton et al. |
| 2002/0165577 A1 | 11/2002 | Witt et al. |
| 2003/0093103 A1 | 5/2003 | Malackowski et al. |
| 2003/0109802 A1 | 6/2003 | Laeseke et al. |
| 2003/0114851 A1 | 6/2003 | Truckai et al. |
| 2004/0097911 A1 | 5/2004 | Murakami et al. |
| 2004/0104260 A1* | 6/2004 | Scher et al. ............ 228/175 |
| 2004/0116952 A1 | 6/2004 | Sakurai et al. |
| 2004/0133189 A1 | 7/2004 | Sakurai |
| 2004/0173487 A1 | 9/2004 | Johnson et al. |
| 2005/0021065 A1 | 1/2005 | Yamada et al. |
| 2005/0033195 A1 | 2/2005 | Fulton, III et al. |
| 2005/0256522 A1 | 11/2005 | Francischelli et al. |
| 2006/0030797 A1 | 2/2006 | Zhou et al. |
| 2006/0079829 A1 | 4/2006 | Fulton, III et al. |
| 2006/0079874 A1 | 4/2006 | Faller et al. |
| 2006/0079877 A1 | 4/2006 | Houser et al. |
| 2006/0079879 A1 | 4/2006 | Faller et al. |
| 2006/0253176 A1 | 11/2006 | Caruso et al. |
| 2007/0027447 A1 | 2/2007 | Theroux et al. |
| 2007/0084742 A1 | 4/2007 | Miller et al. |
| 2007/0103437 A1 | 5/2007 | Rosenberg |
| 2007/0191713 A1 | 8/2007 | Eichmann et al. |
| 2007/0207354 A1 | 9/2007 | Curello et al. |
| 2007/0261978 A1 | 11/2007 | Sanderson |
| 2007/0265613 A1 | 11/2007 | Edelstein et al. |
| 2007/0265620 A1 | 11/2007 | Kraas et al. |
| 2007/0282333 A1 | 12/2007 | Fortson et al. |
| 2008/0003491 A1 | 1/2008 | Yahnker et al. |
| 2008/0004656 A1 | 1/2008 | Livneh |
| 2008/0051723 A1* | 2/2008 | Laermer et al. ............ 604/191 |
| 2008/0057470 A1 | 3/2008 | Levy et al. |
| 2008/0147058 A1 | 6/2008 | Horrell et al. |
| 2008/0150754 A1 | 6/2008 | Quendt |
| 2008/0161783 A1 | 7/2008 | Cao |
| 2008/0173651 A1 | 7/2008 | Ping |
| 2008/0188810 A1 | 8/2008 | Larsen et al. |
| 2008/0200940 A1 | 8/2008 | Eichmann et al. |
| 2008/0221491 A1 | 9/2008 | Slayton et al. |
| 2008/0228104 A1 | 9/2008 | Uber, III et al. |
| 2008/0241679 A1* | 10/2008 | Okutani et al. ............ 429/185 |
| 2008/0255413 A1 | 10/2008 | Zemlok et al. |
| 2008/0281301 A1 | 11/2008 | Deboer et al. |
| 2009/0030437 A1 | 1/2009 | Houser et al. |
| 2009/0043797 A1 | 2/2009 | Dorie et al. |
| 2009/0076506 A1 | 3/2009 | Baker |
| 2009/0105750 A1 | 4/2009 | Price et al. |
| 2009/0125026 A1 | 5/2009 | Rioux et al. |
| 2009/0137952 A1 | 5/2009 | Ramamurthy et al. |
| 2009/0138006 A1 | 5/2009 | Bales et al. |
| 2009/0143797 A1 | 6/2009 | Smith et al. |
| 2009/0143798 A1 | 6/2009 | Smith et al. |
| 2009/0143799 A1 | 6/2009 | Smith et al. |
| 2009/0143800 A1 | 6/2009 | Deville et al. |
| 2009/0143801 A1 | 6/2009 | Deville et al. |
| 2009/0143802 A1 | 6/2009 | Deville et al. |
| 2009/0143803 A1 | 6/2009 | Palmer et al. |
| 2009/0143804 A1 | 6/2009 | Palmer et al. |
| 2009/0143805 A1 | 6/2009 | Palmer et al. |
| 2009/0209979 A1 | 8/2009 | Yates et al. |
| 2009/0209990 A1 | 8/2009 | Yates et al. |
| 2009/0240246 A1 | 9/2009 | Deville et al. |
| 2009/0253030 A1 | 10/2009 | Kooij |
| 2009/0275940 A1 | 11/2009 | Malackowski et al. |
| 2009/0281430 A1 | 11/2009 | Wilder |
| 2009/0281464 A1 | 11/2009 | Cioanta et al. |
| 2010/0016855 A1 | 1/2010 | Ramstein et al. |
| 2010/0021022 A1 | 1/2010 | Pittel et al. |
| 2010/0030218 A1 | 2/2010 | Prevost |
| 2010/0069940 A1 | 3/2010 | Miller et al. |
| 2010/0076455 A1 | 3/2010 | Birkenbach et al. |
| 2010/0081014 A1* | 4/2010 | Tyce et al. ............ 429/2 |
| 2010/0089970 A1 | 4/2010 | Smith et al. |
| 2010/0106144 A1 | 4/2010 | Matsumura et al. |
| 2010/0106146 A1 | 4/2010 | Boitor et al. |
| 2010/0125172 A1 | 5/2010 | Jayaraj |
| 2010/0152610 A1 | 6/2010 | Parihar et al. |
| 2010/0201311 A1 | 8/2010 | Lyell Kirby et al. |
| 2010/0211053 A1 | 8/2010 | Ross et al. |
| 2010/0239908 A1* | 9/2010 | Howard et al. ............ 429/220 |
| 2010/0249665 A1 | 9/2010 | Roche |
| 2010/0268221 A1 | 10/2010 | Beller et al. |

(56) References Cited

U.S. PATENT DOCUMENTS

| | | |
|---|---|---|
| 2010/0274160 A1 | 10/2010 | Yachi et al. |
| 2010/0301095 A1 | 12/2010 | Shelton, IV et al. |
| 2011/0009694 A1 | 1/2011 | Schultz et al. |
| 2011/0015660 A1 | 1/2011 | Wiener et al. |
| 2011/0024479 A1* | 2/2011 | Swensgard et al. ........ 227/176.1 |
| 2011/0058982 A1 | 3/2011 | Kaneko |
| 2011/0077514 A1 | 3/2011 | Ulric et al. |
| 2011/0087218 A1 | 4/2011 | Boudreaux et al. |
| 2011/0152901 A1 | 6/2011 | Woodruff et al. |
| 2011/0224668 A1 | 9/2011 | Johnson et al. |
| 2011/0247952 A1 | 10/2011 | Hebach et al. |
| 2012/0179036 A1 | 7/2012 | Patrick et al. |
| 2012/0265230 A1 | 10/2012 | Laurent et al. |
| 2012/0283732 A1 | 11/2012 | Lam |
| 2012/0292367 A1 | 11/2012 | Morgan et al. |
| 2013/0085330 A1 | 4/2013 | Ramamurthy et al. |
| 2013/0085332 A1 | 4/2013 | Ramamurthy et al. |
| 2013/0085397 A1 | 4/2013 | Ramamurthy et al. |
| 2013/0090528 A1 | 4/2013 | Ramamurthy et al. |
| 2013/0090530 A1 | 4/2013 | Ramamurthy et al. |
| 2013/0090552 A1 | 4/2013 | Ramamurthy et al. |
| 2013/0116690 A1 | 5/2013 | Unger et al. |

FOREIGN PATENT DOCUMENTS

| | | |
|---|---|---|
| EP | 0897696 A1 | 2/1999 |
| EP | 0947167 A1 | 10/1999 |
| EP | 1330991 A1 | 7/2003 |
| EP | 1525853 A2 | 4/2005 |
| EP | 1535585 A2 | 6/2005 |
| EP | 1684396 A2 | 7/2006 |
| EP | 1721576 A1 | 11/2006 |
| EP | 1743592 A1 | 1/2007 |
| EP | 1818021 A1 | 8/2007 |
| EP | 1839599 | 10/2007 |
| EP | 1868275 A2 | 12/2007 |
| EP | 1886637 A1 | 2/2008 |
| EP | 1943976 A2 | 7/2008 |
| EP | 1970014 | 9/2008 |
| EP | 1997493 A2 | 12/2008 |
| EP | 2027819 A1 | 2/2009 |
| EP | 2090256 A2 | 8/2009 |
| EP | 2105104 A2 | 9/2009 |
| EP | 2165660 A2 | 3/2010 |
| EP | 2218409 A1 | 8/2010 |
| EP | 2243439 A1 | 10/2010 |
| EP | 2345454 A1 | 7/2011 |
| GB | 2425874 | 11/2006 |
| GB | 2440566 A | 2/2008 |
| WO | WO 97/24072 | 7/1997 |
| WO | WO 00/65682 | 2/2000 |
| WO | WO 03/013374 | 2/2003 |
| WO | WO 03/020139 | 3/2003 |
| WO | WO 2004/113991 | 12/2004 |
| WO | WO 2005/079915 | 9/2005 |
| WO | WO 2006/023266 | 3/2006 |
| WO | WO 2007/004515 | 1/2007 |
| WO | WO 2007/024983 | 3/2007 |
| WO | WO 2007/090025 | 8/2007 |
| WO | WO 2007/137115 | 11/2007 |
| WO | WO 2007/137304 | 11/2007 |
| WO | WO 2008/071898 | 6/2008 |
| WO | WO 2008/102154 | 8/2008 |
| WO | WO 2008/107902 | 9/2008 |
| WO | WO 2008/131357 | 10/2008 |
| WO | WO 2009/018409 | 2/2009 |
| WO | WO 2009/046394 | 4/2009 |
| WO | WO 2009/070780 | 6/2009 |
| WO | WO 2009/073608 | 6/2009 |
| WO | WO 2010/030850 | 3/2010 |
| WO | WO 2010/096174 | 8/2010 |
| WO | WO 2011/059785 | 5/2011 |
| WO | WO 2011/089270 | 7/2011 |

OTHER PUBLICATIONS

U.S. Appl. No. 13/151,471, filed Jun. 2, 2011, Stulen et al.
U.S. Appl. No. 13/151,481, filed Jun. 2, 2011, Yates et al.
U.S. Appl. No. 13/151,488, filed Jun. 2, 2011, Shelton IV et al.
U.S. Appl. No. 13/151,503, filed Jun. 2, 2011, Madan et al.
U.S. Appl. No. 13/151,509, filed Jun. 2, 2011, Smith et al.
U.S. Appl. No. 13/151,512, filed Jun. 2, 2011, Houser et al.
U.S. Appl. No. 13/151,515, filed Jun. 2, 2011, Felder et al.
U.S. Appl. No. 13/269,870, filed Oct. 10, 2011, Houser et al.
U.S. Appl. No. 13/269,883, filed Oct. 10, 2011, Mumaw et al.
U.S. Appl. No. 13/269,899, filed Oct. 10, 2011, Boudreaux.
U.S. Appl. No. 13/270,667, filed Oct. 11, 2011, Timm et al.
U.S. Appl. No. 13/270,684, filed Oct. 11, 2011, Madan et al.
U.S. Appl. No. 13/270,701, filed Oct. 11, 2011, Johnson et al.
U.S. Appl. No. 13/271,352, filed Oct. 12, 2011, Houser et al.
U.S. Appl. No. 13/271,364, filed Oct. 12, 2011, Houser et al.
U.S. Appl. No. 13/274,480, filed Oct. 17, 2011, Mumaw et al.
U.S. Appl. No. 13/274,496, field Oct. 17, 2011, Houser et al.
U.S. Appl. No. 13/274,507, filed Oct. 17, 2011, Houser et al.
U.S. Appl. No. 13/274,516, filed Oct. 17, 2011, Haberstich et al.
U.S. Appl. No. 13/274,540, filed Oct. 17, 2011, Madam.
U.S. Appl. No. 13/274,805, filed Oct. 17, 2011, Price et al.
U.S. Appl. No. 13/274,830, filed Oct. 17, 2011, Houser et al.
U.S. Appl. No. 13/275,495, field Oct. 18, 2011, Houser et al.
U.S. Appl. No. 13/275,514, filed Oct. 18, 2011, Houser et al.
U.S. Appl. No. 13/275,547, filed Oct. 18, 2011, Houser et al.
U.S. Appl. No. 13/275,563, filed Oct. 18, 2011, Houser et al.
U.S. Appl. No. 13/276,660, filed Oct. 19, 2011, Houser et al.
U.S. Appl. No. 13/276,673, filed Oct. 19, 2011, Kimball et al.
U.S. Appl. No. 13/276,687, filed Oct. 19, 2011, Price et al.
U.S. Appl. No. 13/276,707, filed Oct. 19, 2011, Houser et al.
U.S. Appl. No. 13/276,725, filed Oct. 19, 2011, Houser et al.
U.S. Appl. No. 13/276,745, filed Oct. 19, 2011, Stulen et al.
U.S. Appl. No. 13/277,328, filed Oct. 20, 2011, Houser et al.
Dietz, T. et al., Partially Implantable Vibrating Ossicular Prosthesis, Transducers'97, vol. 1, International Conference on Solid State Sensors and Actuators, (Jun. 16-19, 1997) pp. 433-436 (Abstract).
"System 6 Aseptic Battery System," Stryker (2006) pp. 1-2.
Restriction Requirement dated Dec. 11, 2012 for U.S. Appl. No. 13/151,481.
Office Action Non-Final dated Feb. 15, 2013 for U.S. Appl. No. 13/151,481.
Office Action Final dated Jun. 7, 2013 for U.S. Appl. No. 13/151,481.
Restriction Requirement dated Mar. 13, 2013 for U.S. Appl. No. 13/151,509.
Restriction Requirement dated Feb. 28, 2013 for U.S. Appl. No. 13/270,667.
Office Action Non Final dated Apr. 26, 2013 for U.S. Appl. No. 13/270,667.
Office Action Non-Final dated Dec. 21, 2012 for U.S. Appl. No. 13/274,516.
Restriction Requirement dated Feb. 25, 2013 for U.S. Appl. No. 13/274,540.
Office Action Non-Final dated Apr. 30, 2013 for U.S. Appl. No. 13/274,540.
Office Action Non-Final dated Apr. 1, 2013 for U.S. Appl. No. 13/274,805.
Restriction Requirement dated Apr. 29, 2013 for U.S. Appl. No. 13/274,830.
Restriction Requirement dated Apr. 4, 2013 for U.S. Appl. No. 13/275,495.
Office Action Non-Final dated May 31, 2013 for U.S. Appl. No. 13/275,495.
Office Action Non-Final dated May 17, 2013 for U.S. Appl. No. 13/275,547.
Office Action Non-Final dated Feb. 1, 2013 for U.S. Appl. No. 13/275,563.
Restriction Requirement dated Feb. 6, 2013 for U.S. Appl. No. 13/276,660.

(56) References Cited

OTHER PUBLICATIONS

Office Action Non-Final dated Jun. 3, 2013 for U.S. Appl. No. 13/246,660.
Office Action Non-Final dated Dec. 21, 2012 for U.S. Appl. No. 13/276,673.
Restriction Requirement dated Feb. 6, 2013 for U.S. Appl. No. 13/276,687.
Restriction Requirement dated Feb. 21, 2013 for U.S. Appl. No. 13/276,707.
Office Action Non-Final dated May 6, 2013 for U.S. Appl. No. 13/276,707.
Restriction Requirement dated Feb. 6, 2013 for U.S. Appl. No. 13/276,725.
Restriction Requirement dated Dec. 21, 2012 for U.S. Appl. No. 13/276,745.
Office Action Non-Final dated Apr. 30, 2013 for U.S. Appl. No. 13/276,745.
Office Action Non-Final dated Aug. 6, 2013 for U.S. Appl. No. 13/151,471.
Restriction Requirement dated Jul. 5, 2013 for U.S. Appl. No. 13/151,488.
Restriction Requirement dated Jun. 24, 2013 for U.S. Appl. No. 13/151,509.
Office Action Final dated Aug. 16, 2013 for U.S. Appl. No. 13/274,516.
Office Action Final dated Sep. 12, 2013 for U.S. Appl. No. 13/274,805.
Office Action Non-Final dated Jun. 14, 2013 for U.S. Appl. No. 13/274,830.
Office Action Final dated Aug. 29, 2013 for U.S. Appl. No. 13/275,563.
Office Action Non Final dated Aug. 19, 2013 for U.S. Appl. No. 13/276,673.
Office Action Non-Final dated Jun. 12, 2013 for U.S. Appl. No. 13/276,687.
Notice of Allowance dated Dec. 6, 2013 for U.S. Appl. No. 13/151,471.
Office Action Non-Final dated Sep. 26, 2013 for U.S. Appl. No. 13/151,509.
Office Action Final dated Oct. 25, 2013 for U.S. Appl. No. 13/270,667.
Office Action Non-Final dated Nov. 21, 2013 for U.S. Appl. No. 13/271,352.
Office Action Non-Final dated Dec. 6, 2013 for U.S. Appl. No. 13/274,516.
Office Action Final dated Oct. 25, 2013 for U.S. Appl. No. 13/274,540.
Office Action Final dated Nov. 26, 2013 for U.S. Appl. No. 13/274,830.
Office Action Final dated Dec. 5, 2013 for U.S. Appl. No. 13/275,495.
Notice of Allowance dated Nov. 12, 2013 for U.S. Appl. No. 13/276,687.
Office Action Final dated Sep. 27, 2013 for U.S. Appl. No. 13/276,707.
Office Action Final dated Nov. 8, 2013 for U.S. Appl. No. 13/276,745.
Office Action Non-Final dated Mar. 28, 2014 for U.S. Appl. No. 13/151,471.
Office Action Non Final dated Jun. 18, 2014 for U.S. Appl. No. 13/151,503.
Office Action Final dated Jan. 29, 2014 for U.S. Appl. No. 13/151,509.
Restriction Requirement dated Jun. 11, 2014 for U.S. Appl. No. 13/151,512.
Office Action Non-Final dated Feb. 14, 2014 for U.S. Appl. No. 13/274,480.
Restriction Requirement dated Dec. 9, 2013 for U.S. Appl. No. 13/274,496.
Office Action Non-Final dated Feb. 6, 2014 for U.S. Appl. No. 13/274,496.
Office Action Final dated May 15, 2014 for U.S. Appl. No. 13/274,496.
Restriction Requirement dated Mar. 28, 2014 for U.S. Appl. No. 13/274,507.
Office Action Non-Final dated Jun. 19, 2014 for U.S. Appl. No. 13/274,507.
Office Action Final dated Jun. 12, 2014 for U.S. Appl. No. 13/274,516.
Office Action Non Final dated Jan. 6, 2014 for U.S. Appl. No. 13/275,514.
Office Action Final dated Feb. 28, 2014 for U.S. Appl. No. 13/275,547.
Office Action Final dated Mar. 21, 2014 for U.S. Appl. No. 13/276,673.
Notice of Allowance dated Jun. 2, 2014 for U.S. Appl. No. 13/276,687.
Office Action Non-Final dated Feb. 28, 2014 for U.S. Appl. No. 13/276,745.
International Search Report and Written Opinion dated Jan. 26, 2012 for Application No. PCT/US2011/059212.
International Search Report and Written Opinion dated Feb. 2, 2012 for Application No. PCT/US2011/059378.
International Search Report dated Feb. 2, 2012 for Application No. PCT/US2011/059354.
International Search Report dated Feb. 7, 2012 for Application No. PCT/US2011/059351.
International Search Report dated Feb. 13, 2012 for Application No. PCT/US2011/059217.
International Search Report dated Feb. 23, 2012 for Application No. PCT/US2011/059371.
International Search Report dated Mar. 15, 2012 for Application No. PCT/US2011/059338.
International Search Report dated Mar. 22, 2012 for Application No. PCT/US2011/059362.
International Search Report dated Apr. 4, 2012 for Application No. PCT/US2011/059215.
International Search Report dated Apr. 11, 2012 for Application No. PCT/US2011/059381.
International Search Report dated May 24, 2012 for Application no. PCT/US2011/059378.
International Search Report dated Jun. 4, 2012 for Application No. PCT/US2011/059365.
International Search Report dated Jun. 12, 2012 for Application No. PCT/US2011/059218.
Communication from International Searching Authority dated Feb. 6, 2012 for Application.No. PCT/US2011/059362.
Communication from International Searching Authority dated Feb. 2, 2012 for Application.No. PCT/US2011/059222.
Communication from International Searching Authority dated Jan. 24, 2012 for Application.No. PCT/US2011/059215.
Communication from International Searching Authority dated Feb. 2, 2012 for Application No. PCT/US2011/059378.
Machine Translation of the Abstract of German Application No. DE 102009013034, (Oct. 7, 2010).
Machine Translation of German Application No. DE 102008051866, (Jan. 7, 2010).
International Search Report dated Jan. 26, 2012 for Application No. PCT/US2011/059220.
International Search Report dated Apr. 18, 2012 for Application No. PCT/US2011/059222.
International Search Report dated Jan. 12, 2012 for Application No. PCT/US2011/059226.
International Search Report dated May 29, 2012 for Application No. PCT/US2011/059358.
International Search Report and Written Opinion dated Jul. 6, 2012 for Application No. PCT/US2011/059381.
EP Communication dated Feb. 19, 2014 for Application No. EP 11781972.2.
International Preliminary Report on Patentability dated May 7, 2013 for Application No. PCT/US2011/059212.

(56) References Cited

OTHER PUBLICATIONS

International Preliminary Report on Patentability dated May 8, 2013 for Application No. PCT/US2011/059215.
International Preliminary Report on Patentability dated May 7, 2013 for Application No. PCT/US2011/059217.
International Preliminary Report on Patentability dated May 7, 2013 for Application No. PCT/US2011/059218.
International Preliminary Report on Patentability dated May 7, 2013 for Application No. PCT/US2011/059220.
International Preliminary Report on Patentability dated May 7, 2013 for Application No. PCT/US2011/059222.
International Preliminary Report on Patentability dated Feb. 1, 2012 for Application No. PCT/US2011/059223.
International Preliminary Report on Patentability dated May 7, 2013 for Application No. PCT/US2011/059226.
International Preliminary Report on Patentability dated May 7, 2013 for Application No. PCT/US2011/059338.
International Preliminary Report on Patentability dated May 7, 2013 for Application No. PCT/US2011/059351.
International Preliminary Report on Patentability dated May 7, 2013 for Application No. PCT/US2011/059354.
International Preliminary Report on Patentability dated May 7, 2013 for Application No. PCT/US2011/059358.
International Preliminary Report on Patentability dated May 7, 2013 for Application No. PCT/US2011/059362.
International Preliminary Report on Patentability dated May 8, 2013 for Application No. PCT/US2011/059365.
International Preliminary Report on Patentability dated May 7, 2013 for Application No. PCT/US2011/059371.
International Preliminary Report on Patentability dated May 7, 2013 for Application No. PCT/US2011/059378.
International Preliminary Report on Patentability dated May 8, 2013 for Application No. PCT/US2011/059381.
US Office Action, Notice of Allowance, dated Aug. 19, 2014 for U.S. Appl. No. 13/151,471.
US Office Action, Non-Final, dated Aug. 14, 2014 for U.S. Appl. No. 13/151,481.
US Office Action, Non-Final, dated Jul. 9, 2014 for U.S. Appl. No. 13/151,509.
US Office Action, Restriction Requirement, dated Jul. 11, 2014 for U.S. Appl. No. 13/269,780.
US Office Action, Non-Final, dated Jul. 29, 2014 for U.S. Appl. No. 13/270,667.
US Office Action, Restriction Requirement, dated Sep. 11, 2014 for U.S. Appl. No. 13/270,701.
US Office Action, Restriction Requirement, dated Sep. 25, 2014 for U.S. Appl. No. 13/270,701.
US Office Action, Restriction Requirement, dated Jul. 9, 2014 for U.S. Appl. No. 13/270,684.
US Office Action, Non Final, dated Oct. 9, 2014 for U.S. Appl. No. 13/270,684.
US Office Action, Restriction Requirement, dated Oct. 2, 2013 for U.S. Appl. No. 13/274,480.
US Office Action, Final, dated Jul. 17, 2014 for U.S. Appl. No. 13/274,480.
US Office Action, Final, dated Aug. 22, 2014 for U.S. Appl. No. 13/274,496.
US Office Action, Non-Final, dated Oct. 8, 2014 for U.S. Appl. No. 13/274,516.
US Office Action, Non-Final, dated Aug. 26, 2014 for U.S. Appl. No. 13/274,540.
US Office Action, Non-Final, dated Aug. 14, 2014 for U.S. Appl. No. 13/274,805.
US Office Action, Non-Final, dated Oct. 22, 2014 for U.S. Appl. No. 13/274,830.
US Office Action, Non-Final, dated Sep. 9, 2014 for U.S. Appl. No. 13/275,514.
US Office Action, Non-Final, dated Aug. 20, 2014 for U.S. Appl. No. 13/275,547.
US Office Action, Non-Final, dated Oct. 23, 2014 for U.S. Appl. No. 13/275,563.
US Office Action, Restriction Requirement, dated Jul. 9, 2014 for U.S. Appl. No. 13/276,660.
US Office Action, Non-Final, dated Aug. 14, 2014 for U.S. Appl. No. 13/276,673.
US Office Action, Notice of Allowance, dated Sep. 12, 2014 for U.S. Appl. No. 13/276,687.
US Office Action, Non-Final, dated Aug. 20, 2014 for U.S. Appl. No. 13/276,725.
US Office Action, Notice of Allowance, dated Oct. 7, 2014 for U.S. Appl. No. 13/276,745.
US Office Action, Restriction Requirement, dated Sep. 24, 2014 for U.S. Appl. No. 13/277,328.
US Office Action, Non-Final, dated Nov. 7, 2014 for U.S. Appl. No. 13/151,488.
US Office Action, Non-Final, dated Nov. 6, 2014 for U.S. Appl. No. 13/151,503.
US Office Action, Notice of Allowance, dated Oct. 28, 2014 for U.S. Appl. No. 13/151,509.
US Office Action, Notice of Allowance, dated Oct. 29, 2014 for U.S. Appl. No. 13/151,512.

* cited by examiner

STERILE HOUSING FOR NON-STERILE MEDICAL DEVICE COMPONENT

PRIORITY

This application claims priority to U.S. Provisional Application Ser. No. 61/410,603, filed Nov. 5, 2010, entitled "Energy-Based Surgical Instruments," the disclosure of which is incorporated by reference herein.

This application also claims priority to U.S. Provisional Application Ser. No. 61/487,846, filed May 19, 2011, entitled "Energy-Based Surgical Instruments," the disclosure of which is incorporated by reference herein.

BACKGROUND

Many medical devices require a power source to function properly. In some cases, medical devices may be plugged into a wall outlet to receive power. However, tethering a medical device to a wall outlet may be cumbersome or difficult to maneuver for the user. In other scenarios, medical devices may be connected to an intermediate power supply or other piece of capital equipment located between the medical device and a wall outlet. Using such an intermediate power source may also be cumbersome and difficult. Furthermore, in many situations, such medical devices must remain sterile; otherwise a patient may be susceptible to infection or other contamination from being exposed to a non-sterile device. Battery packs could be used with such medical devices. However, such battery packs may be non-sterile. Thus, using a battery could pose increased risks to a patient. In the event that a non-sterile battery is used, the non-sterile medical device may ultimately become exposed to the battery, which may compromise the sterility of the medical device for use with a patient. In short, using a non-sterile power source with a sterile medical device may pose a variety of risks.

Merely exemplary devices that rely on electrical power are disclosed in U.S. Pat. No. 6,500,176, entitled "Electrosurgical Systems and Techniques for Sealing Tissue," issued Dec. 31, 2002; U.S. Pat. No. 7,416,101, entitled "Motor-Driven Surgical Cutting and Fastening Instrument with Loading Force Feedback," issued Aug. 26, 2008; U.S. Pat. No. 7,738,971, entitled "Post-Sterilization Programming of Surgical Instruments," issued Jun. 15, 2010; U.S. Pub. No. 2009/0209990, entitled "Motorized Surgical Cutting and Fastening Instrument Having Handle Based Power Source," published Aug. 20, 2009 (now U.S. Pat. No. 8,657,174); U.S. Pub. No. 2006/0079874, entitled "Tissue Pad for Use with an Ultrasonic Surgical Instrument," published Apr. 13, 2006 (now abandoned); U.S. Pub. No. 2007/0191713, entitled "Ultrasonic Device for Cutting and Coagulating," published Aug. 16, 2007 (now abandoned); U.S. Pub. No. 2007/0282333, entitled "Ultrasonic Waveguide and Blade," published Dec. 6, 2007 (now abandoned); U.S. Pub. No. 2008/0200940, entitled "Ultrasonic Device for Cutting and Coagulating," published Aug. 21, 2008 (now abandoned). The disclosure of each of the above-cited U.S. patents and U.S. patent Application Publications is incorporated by reference herein.

While several systems and methods have been made for use with an electrically powered medical device, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements. In the drawings some components or portions of components are shown in phantom as depicted by broken lines.

Figure 1:
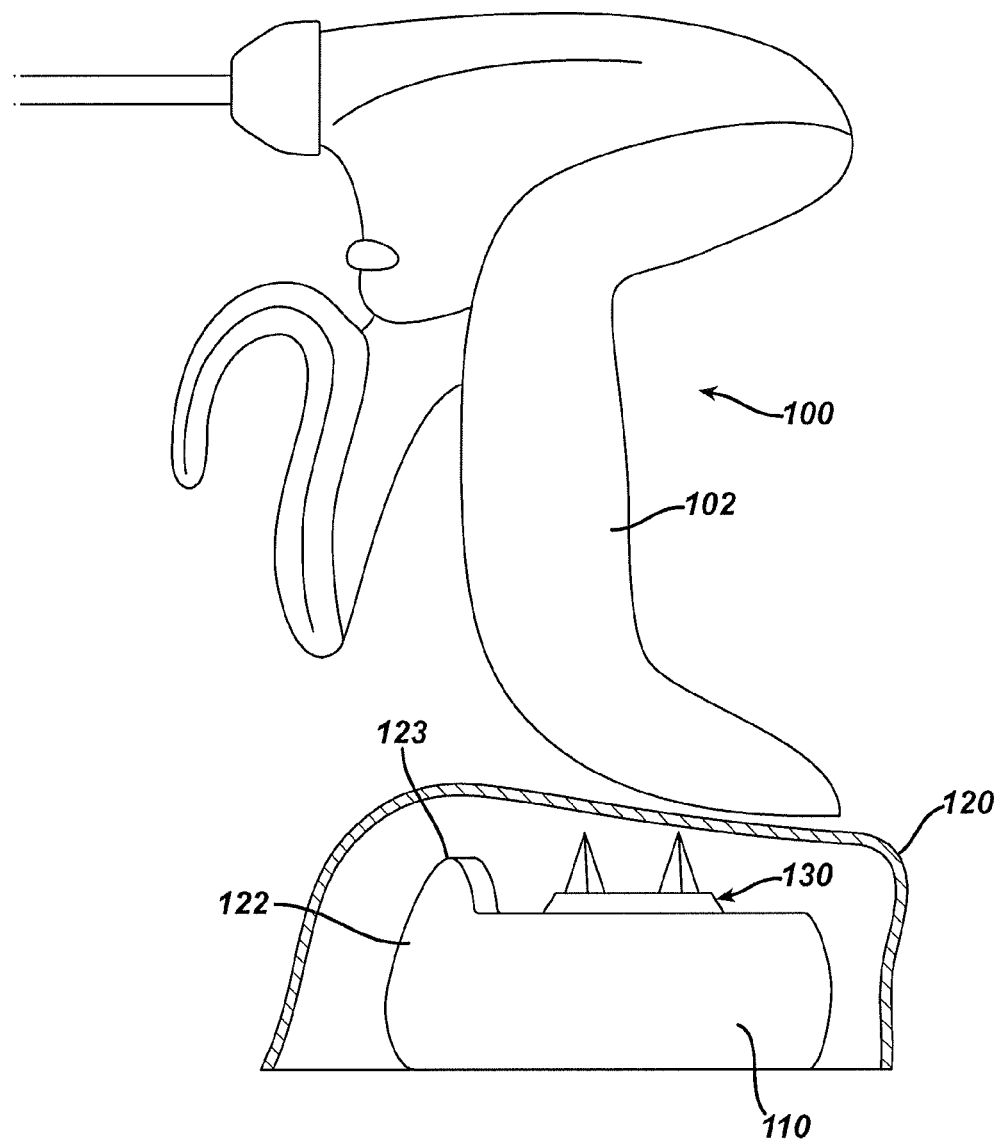
FIG. 1 depicts a side view of an exemplary connection feature with a sterilized medical device and a battery pack.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

I. Overview

In association with surgical or other medical procedures, it will be appreciated that medical devices that may be exposed to a patient or medical personnel will need to be sterilized. Furthermore, while a medical device may be initially sterilized, in many situations, the medical device will need to remain sterilized until the start of, and in some cases, during the procedure.

It will also be appreciated that in some cases, electrically powered medical devices may be used. For example, such medical devices are shown and referenced in U.S. Pat. No. 6,500,176, U.S. Pat. No. 7,416,101, U.S. Pat. No. 7,738,971, U.S. Pub. No. 2009/0209990 (now U.S. Pat. No. 8,657,174), U.S. Pub. No. 2006/0079874 (now abandoned), U.S. Pub. No. 2007/0191713 (now abandoned), U.S. Pub. No. 2007/0282333 (now abandoned), and U.S. Pub. No. 2008/0200940 (now abandoned). With some electrically power medical devices, a direct cable between the medical device and an outlet may be used. In other cases, a piece of capital equipment may be positioned between the medical device and the outlet, which, by way of example only, may be used to serve as a transformer and/or to condition power/control signals to the medical device. However, it will be appreciated that a more portable electrically powered medical device may be desirable. As such, rather than a direct line to an outlet, a battery and/or battery pack may be used with the electrically powered medical device, which may enable a user to have greater mobility as the medical device is not tethered to a wall or piece of capital equipment.

Since a battery may not be sterile in some instances, it will be appreciated that housing the battery in a manner that prevents exposure of the potentially non-sterile battery to the medical device to be used in the procedure may be desirable. It will further be appreciated that as a battery is transported, stored, or charged for use, the battery may be subject to some level of contamination, thereby causing the battery to be non-sterile. Furthermore, as a battery travels, it will be appreciated that leaving a battery in a disconnected state may be desirable for instance, for safety reasons or to prevent inadvertent discharge of the battery prior to the time that the battery is intended to be used.

In general, a medical device may be used with a battery pack. For example, it will be appreciated that devices such as those shown in U.S. Pat. No. 6,500,176, U.S. Pat. No. 7,416, 101, U.S. Pat. No. 7,738,971, U.S. Pub. No. 2009/0209990 (now U.S. Pat. No. 8,657,174), U.S. Pub. No. 2006/0079874 (now abandoned), U.S. Pub. No. 2007/0191713 (now abandoned), U.S. Pub. No. 2007/0282333 (now abandoned), or U.S. Pub. No. 2008/0200940 (now abandoned) may be modified for use with a battery pack rather than being powered by a cable plugged into an outlet or capital equipment. A portion of the battery pack may be connected to a connection device, such as will be described in further detail below. Generally speaking, the battery pack, which will be non-sterile in some instances, may be enclosed in a membrane or case. The outer surface of the membrane or case may be sterile, while the inside or inner surface may be sterile or non-sterile. It will be appreciated that through use of the membrane or case along with the connection device, the battery pack may be connected to the sterile medical device without compromising the sterility of the medical device. Various examples will be described in greater detail below, while other examples will be apparent to those of ordinary skill in the art in view of the teachings herein. While many examples described herein relate to battery packs, it should be understood that the teachings may also be applied to various other kinds of components. By way of example only, the teachings herein relating to battery packs may be readily applied to replaceable circuit boards, on-board control modules, or other modular or otherwise replaceable components of a medical device or other related medical components.

It should be understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should also be understood that various teachings herein may be readily combined with various teachings in any of the following patent applications, all of which are filed on even date herewith and the disclosures of all of which are incorporated by reference herein: U.S. patent application Ser. No. 13/151,471 (published as U.S. Pub. No. 2012/0112690), entitled "Medical Device Packaging with Charging Interface"; U.S. patent application Ser. No. 13/151,481 (published as U.S. Pub. No. 2012/0116379), entitled "Motor Driven Electrosurgical Device with Mechanical and Electrical Feedback," published May 10, 2012; U.S. patent application Ser. No. 13/151,503 (published as U.S. Pub. No. 2012/0116380), entitled "Sterile Medical Instrument Charging Device," published May 10, 2012; U.S. patent application Ser. No. 13/151, 509 (published as U.S. Pub. No. 2012/0110824), entitled "Medical Device Packaging with Window for Insertion of Reusable Component," published May 10, 2012; U.S. patent application Ser. No. 13/151,512 (published as U.S. Pub. No. 2012/0110810), entitled "Medical Device with Feature for Sterile Acceptance of Non-Sterile Reusable Component," published May 10, 2012; and U.S. patent application Ser. No. 13/151,515 (published as U.S. Pub. No. 2012/0305427), entitled "Sterile Package System for Medical Device," published Dec. 6, 2012. Various suitable ways in which teachings herein may be combined with teachings of the above-referenced patent applications, as well as various ways in which teachings of the above-referenced patent applications may be combined together with or without teachings herein, will be apparent to those of ordinary skill in the art.

II. Connection Feature

FIG. 1 depicts one merely exemplary version of an instrument (100) for use with a battery pack (110). In the illustrated version, battery pack (110) is surrounded by a bag (120). A connection feature (130) is attached to battery pack (110).

Instrument (100) comprises a handle portion (102), which may be engaged by a user. Handle portion (102) has a pistol grip configuration such that the user may grasp handle portion (102) during use of instrument (100). It will be appreciated that use of a pistol grip for handle portion (102) is merely exemplary and other shapes for handle portion (102) may be used. Furthermore, in other versions, instrument (100) may have a shape or construction where the user does not grip instrument (100) at all. By way of example only, instrument (100) may be constructed in accordance with at least some of the teachings of U.S. Pat. No. 6,500,176, U.S. Pat. No. 7,416, 101, U.S. Pat. No. 7,738,971, U.S. Pub. No. 2009/0209990 (now U.S. Pat. No. 8,657,174), U.S. Pub. No. 2006/0079874 (now abandoned), U.S. Pub. No. 2007/0191713 (now abandoned), U.S. Pub. No. 2007/0282333 (now abandoned), or U.S. Pub. No. 2008/0200940 (now abandoned). Indeed, various suitable ways in which the teachings herein may be incorporated with the teachings in those patent and publication references will be apparent to those of ordinary skill in the art.

Connection feature (130) is attached to battery pack (110). In some versions, connection feature (130) may be connected to and/or integrally formed with battery pack (110). In some other versions, connection feature (130) and battery pack (110) may be of uniform construction. Other suitable relationships between connection feature (130) and battery pack (110) will be apparent to one of ordinary skill in the art in view of the teachings herein.

Battery pack (110) with connection feature (130) attached is positioned within bag (120). Bag (120) may comprise generally a protective sleeve, a protective film bag, or any other suitable covering as would be apparent to one of ordinary skill in the art in view of the teachings herein. In the illustrated version, bag (120) comprises a flexible material such that battery back (110) may be easily placed in bag (120). Bag (120) comprises a sterile outer surface such that the outer surface of bag (120) may come into contact with instrument (100) without contaminating instrument (100) when bag (120) contains battery pack (110), even if battery pack (110) is non-sterile. In some versions, bag (120) may be attached to battery pack (110) using a clip or snap coupling between bag (120) and battery pack (110). In other versions, bag (120) and battery pack (110) need not be coupled together. In some versions, bag (120) fully encompasses and is sealed about battery pack (110), though it should be understood that bag (120) need not necessarily be sealed and/or fully encompass battery pack (120). For instance, bag (120) could merely encompass connection feature (130) and/or other portions of battery pack (110) that come into contact with or otherwise come into close proximity with instrument (100).

Battery pack (110) comprises a housing (122) to hold batteries or other portable power sources. Batteries may comprise lithium ion batteries (e.g., prismatic cell type of lithium ion batteries, etc.), alkaline batteries, nickel cadmium batteries, or any other power sources which will be apparent to one of ordinary skill in the art in view of the teachings herein.

Figure 2:
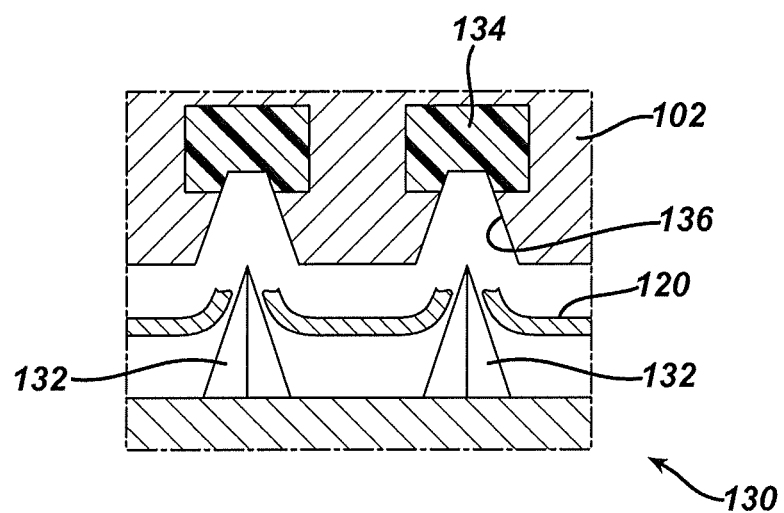
FIG. 2 depicts a partial side, cross-sectional view of the connection feature of FIG. 1.

As stated above, connection feature (130) is connected to battery pack (110). A closer view of connection feature (130) is shown in FIG. 2. Connection feature (130) is able to engage handle portion (102) of instrument (100) to thereby supply electrical power to instrument (100). For instance, battery pack (110) may selectively latch with or otherwise couple with handle portion (102), with connection device (130) positioned to couple with electrical components of instrument (100) as described in greater detail below.

Connection feature (130) comprises a pair of electrodes (132) extending upwardly from the top of connection feature (130). Each electrode (132) comprises a sharp tip such that pair of electrodes (132) can puncture bag (120). It will be appreciated that bag (120) comprises an elastic material capable of deformation such that when pair of electrodes (132) push against bag (120), bag (120) deforms prior to puncturing. It will be appreciated that by first stretching and deforming prior to puncturing bag (120), bag (120) clings to pair of electrodes (132), which enables bag (120) and electrodes (132) to form a seal. By clinging to electrodes (132), bag (120) maintains isolation of the non-sterile nature of battery pack (110). In other words, handle portion (102) and instrument (100) will not compromise sterility by engaging connection feature (130) with handle portion (102). It will be appreciated that the elasticity of bag (120) may be associated with a stretch rate of the material from which bag (120) is constructed. In some versions, the height of electrodes (132) may be selected to be twice the per minute stretch rate of the material that bag (120) from which bag is constructed. Once connection feature (130) engages handle portion (102), then electrodes (132) engage at contacts (134) by positioning electrodes (132) within respective contact cavities (136). Additionally, as mentioned above, bag (120) may be coupled to battery pack (110). As a result, bag (120) is connected such that bag (120) is taut over connection feature (130). Thus, if instrument (100) is pressed against connection feature (130), bag (120) will be punctured by electrodes (132) rather than simply bunch up and mold to the shape of electrodes (132). However any suitable length for electrodes (132) may be used as would be apparent to one of ordinary skill in the art in view of the teachings herein.

In the present example, housing (122) includes a raised region (123) near connection feature (130). In some versions, raised region (123) provides a stand-off that is configured to space bag (120) away from electrodes (132), thereby reducing the risk of premature puncture of bag (120) by electrodes (132). Such a stand-off feature may extend around the entire perimeter of connection feature (130). It should also be understood that a stand-off may be configured with a height that is high enough to space bag (120) away from electrodes (132) yet that is also low enough to allow electrodes (132) to penetrate bag (120) when battery pack (110) and handle portion (102) are pushed together. In addition or in the alternative, prior to using battery pack (110) and connection feature (130), a removable cap may be placed over connection feature (130), which may be later removed when the user is ready to use battery pack (110), such as by removing the removable cap from connection feature (130) by manipulating the removable cap through bag (120) prior to use. In some other versions, connection feature (130) may be constructed to be retractable such that the user may press a firing button to cause electrodes (132) to selectively extend from connection feature (130) prior to use. In addition or in the alternative, an electrode firing mechanism (132) may include a trigger that is activated upon coupling of battery pack (110) with instrument (100), such that electrodes (132) are retracted until battery pack (110) is coupled with instrument (100), whereupon electrodes (132) fire through bag (120) and into contacts (134). Other suitable variations of connection feature (130) will be apparent to one of ordinary skill in the art in view of the teachings herein.

To facilitate shipping, handling and storage of devices designed with penetrating features such as electrodes (132), shipping and handling containers may prevent the penetrating features from premature function. Within a secondary sterile pouch or enclosure, a removable, rigid or semi-rigid cap would be one way to create mechanical isolation of the penetrating features. Another method would be to include a shim with depressions or holes to hide the penetrating features. The shim could be attached either with a mechanical retention method such as a clip or catch, or alternately with a peelable adhesive with light tack strength. Other suitable ways in which a penetrable container such as bag (120) may be substantially protected from puncture or other damage by penetrating features such as electrodes (132) will be apparent to those of ordinary skill in the art in view of the teachings herein.

Each contact (134) comprises a conductive foam material in the present example, such that electrodes (132) can penetrate at least a corresponding contact (134) to establish electrical communication between electrodes (132) and instrument (100). Furthermore, since electrodes (132) is in electrical communication with batteries contained in battery pack (110), by engaging electrodes (132) with contacts (134), battery pack (110) can provide power to instrument (100).

The shape of electrodes (132) is such that it complements contact cavities (136) positioned within handle portion (102). In the exemplary version, each electrode (132) comprises a conical shape operable to puncture bag (120). Accordingly, each contact cavity (136) comprises a generally hollowed out frusto-conical shape. It will be appreciated that the inwardly sloped shape of contact cavity (136) helps to seat and/or guide electrodes (132) into each contact cavity (136) to reach the respective contact (134). Furthermore, it will be appreciated that the sloped shape of each contact cavity (136) aids in promoting puncturing of bag (120). However, electrodes (132) and contact cavities (136) may comprise any suitable shape to puncture bag (120) and provide an electrical connection between contacts (134) and electrodes (132) as would be apparent to one of ordinary skill in the art in view of the teachings herein. Furthermore, in the exemplary illustrated version, connection feature (130) comprises two electrodes (132), but any suitable number of electrodes (132) may be used as would be apparent to one of ordinary skill in the art in view of the teachings herein.

Thus, in use, a user may insert battery pack (110) into bag (120) where the outside of bag (120) is sterile. Bag (120) may then be pressed up against handle portion (102) to roughly align electrodes (132) with contacts (134). The user may then press battery pack (110) and handle portion (102) together such that electrodes (132) puncture bag (120). Electrodes (132) then establish electrical communication with contacts (134) such that battery pack (110) can deliver electrical power to instrument (100). Furthermore, battery pack (110) may be attached to handle portion (102) of instrument (100) through one or more latches and/or other features able to support the weight of battery pack (110) such that instrument (100) may be lifted with battery pack (110) attached to handle portion (102). In some versions, bag (120) may comprise thinner regions for controlling where bag (120) will puncture when pressured by electrodes (132). Though handle portion (102) is pressed against battery pack (110), battery pack (110), which may be non-sterile, does not contaminate handle portion (102) since bag (120), which is sterile, is sandwiched between battery pack (110) and handle portion (102), thereby providing a protective layer. It will be appreciated that the only portion of connection feature (130) to come in contact with instrument (100) will be electrodes (132) by way of contacts (134) in the present example. As a result, the user can use battery pack (110), which may not be sterile, with instrument (100) that has been sterilized, without compromising the sterility of instrument (100).

III. Sterile Barrier

Figure 3:
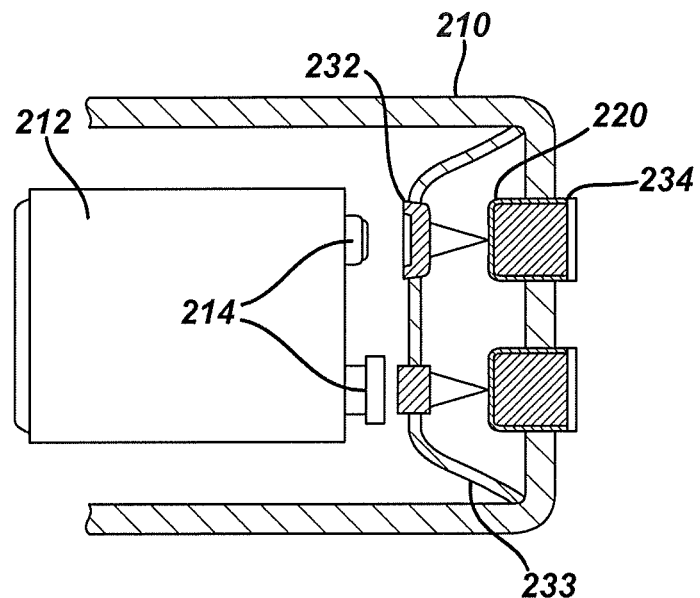
FIG. 3 depicts a side, partially cross sectional view of an exemplary alternative version of a connection feature for a sterilized medical device.
Figure 4:
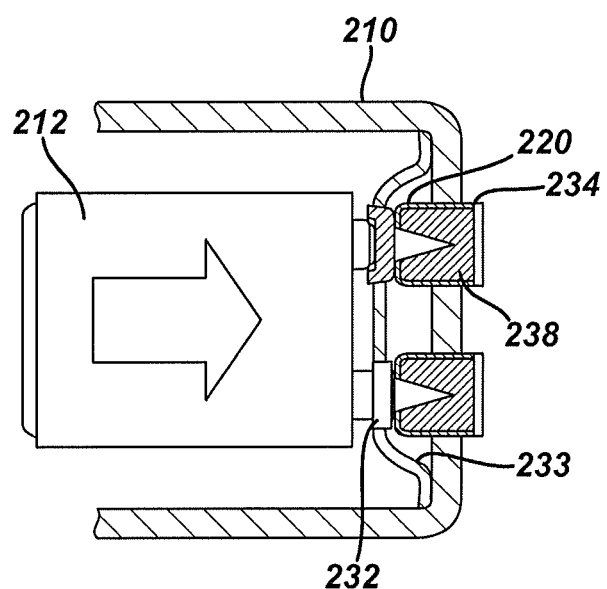
FIG. 4 depicts a side, partially cross sectional view of the connection feature of FIG. 3 engaging electrical contacts for a sterilized medical device.

It will be appreciated that other variations for powering a tool or other medical device with a non-sterile battery may be used. FIGS. 3-4 depict one such alternative version by making use of a sterile barrier thereby allowing a non-sterile battery to be shipped, charged, and later assembled in a sterile environment in preparation for use without compromising the sterility of other items in the sterile environment.

FIGS. 3-4 show a compartment (210), which may be used to house a battery (212). Battery (212) of this example comprises two posts (214), which can engage a pair of electrodes (232). Battery (212) may comprise a standard alkaline or lithium ion type battery. Furthermore, battery (212) may comprise any type of power source as would be apparent to one of ordinary skill in the art in view of the teachings herein. While battery (212) of the present example comprises a generally rectangular shape with two posts (214), any suitable number of posts may be used as would be apparent to one of ordinary skill in the art in view of the teachings herein. It will be appreciated that in some versions, battery (212) is not sterile; yet battery (212) may still be used with a sterile medical device through use of a sterile barrier (220), without compromising the sterility of the medical device.

Electrodes (232) each comprise a spike shaped projection. Furthermore, electrodes (232) are positioned to face a sterile barrier (220). Electrodes (232) may of course comprise any suitable shape such that electrodes (232) can puncture sterile barrier (220), which will result ultimately in establishing an electrical connection between battery (212) and a medical device to be powered. Electrodes (232) are held in place by a collapsible web (233), which is able to resiliently support electrodes (232) until a later time when battery (212) is ready to deliver power to a medical device. As shown in the exemplary version, web (233) holds electrodes (232) directly facing electrical contacts (234) without creating a contact between electrodes (232) and sterile barrier (220). Web (233) comprises an electrically insulated material that is resiliently biased to keep electrodes (232) spaced away from contacts (234) in the present example. As a result, it will be appreciated that in the exemplary version, even if posts (214) are coupled with electrodes (232), battery (212) will not discharge without electrodes (232) being in communication with contacts (234). Thus, battery (212) may retain maximum charge prior to use. When power is needed from battery (212), battery (212) may be pushed toward contacts (234) to collapse web (233) and place electrodes (232) in communication with contacts (234).

Sterile barrier (220) envelops a conduction foam (238), which leads to electrical contacts (234) in direct communication with a medical device to be locally powered. In the illustrated version, conduction foam (238) extends through the wall of compartment (210). Compartment (210) may be part of a battery reception recess in a medical device that is constructed in accordance with at least some of the teachings of U.S. Pat. No. 6,500,176, U.S. Pat. No. 7,416,101, U.S. Pat. No. 7,738,971, U.S. Pub. No. 2009/0209990 (now U.S. Pat. No. 8,657,174), U.S. Pub. No. 2006/0079874 (now abandoned), U.S. Pub. No. 2007/0191713 (now abandoned), U.S. Pub. No. 2007/0282333 (now abandoned), or U.S. Pub. No. 2008/0200940 (now abandoned). In the present example, barrier (220) envelops two portions of conduction foam (238), which correspond to two electrodes (232). However, any suitable number of portions of conduction foam (238) may be used as would be apparent to one of ordinary skill in the art. For example, barrier (220) could envelop just one large portion of conduction foam (238). Furthermore, barrier (220) could envelop many more portions of conduction foam (238) than electrodes (232). Barrier (220) may comprise thick-walled portions with thinner-walled puncture points being positioned at the points where electrodes (232) will breach barrier (220). Barrier (220) comprises an elastic material such that when barrier (220) is punctured and breached by electrodes (232), barrier (220) maintains a seal about electrodes (232) so as to maintain sterility of the medical device. In the illustrated version, barrier (220) fits snugly around conduction foam (238). As can be seen in FIG. 4, battery (212) may be pressed against electrodes (232), where after connecting battery (212) to electrodes (232), further pressure causes web (233) to collapse and thereby forces electrodes through barrier (220). As barrier (220) is breached, barrier (220) maintains a tight fit around electrodes (232). Electrodes (232) are pushed through conduction foam (238) to engage contacts (234). It will be appreciated that since conduction foam (238) is used, conduction foam (238) will also provide electrical communication between electrodes (232) and contacts (234). It should therefore be understood that electrodes (232) need not necessarily come in direct contact with contacts (234) since conduction foam (238) alone may provide the necessary electrical communication with contacts (234).

Once electrodes (232) engage contacts (234), battery (212) then supplies power to the electrically powered medical device, without compromising the sterility of the medical device despite the non-sterility of battery (212). It should be understood that these components may be readily incorporated into any of the devices shown in U.S. Pat. No. 6,500,176, U.S. Pat. No. 7,416,101, U.S. Pat. No. 7,738,971, U.S. Pub. No. 2009/0209990 (now U.S. Pat. No. 8,657,174), U.S. Pub. No. 2006/0079874 (now abandoned), U.S. Pub. No. 2007/0191713 (now abandoned), U.S. Pub. No. 2007/0282333 (now abandoned), or U.S. Pub. No. 2008/0200940 (now abandoned).

IV. Clamshell Compartment

Figure 5:
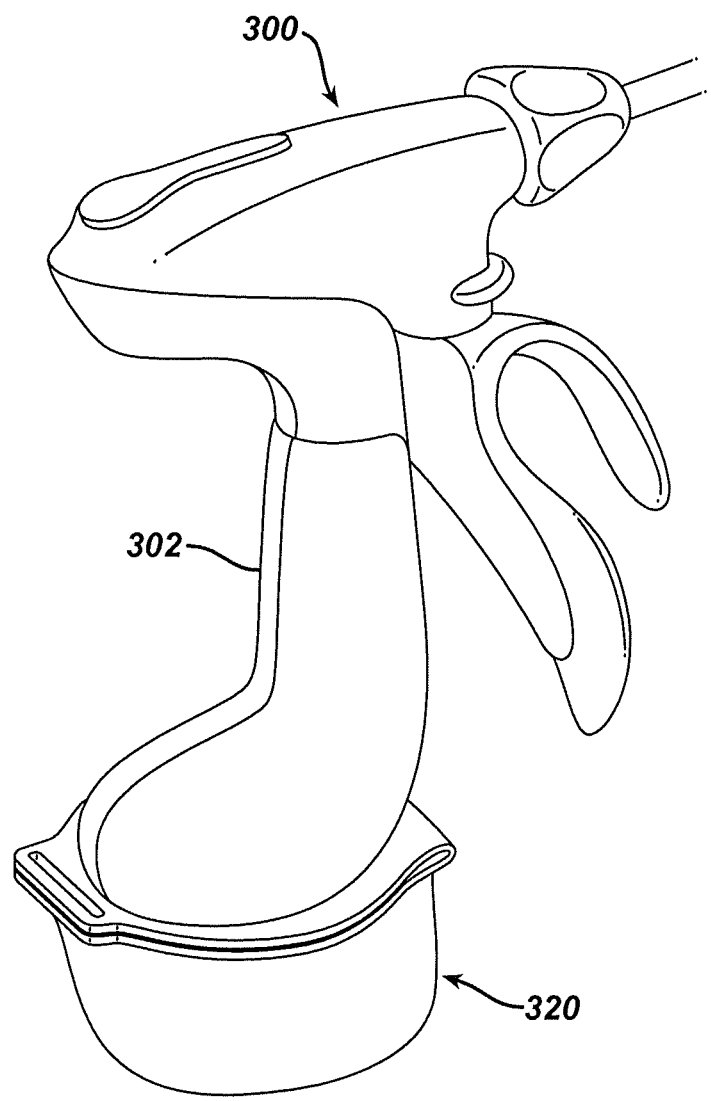
FIG. 5 depicts a perspective view of a compartment with a sterilized medical device.
Figure 6:
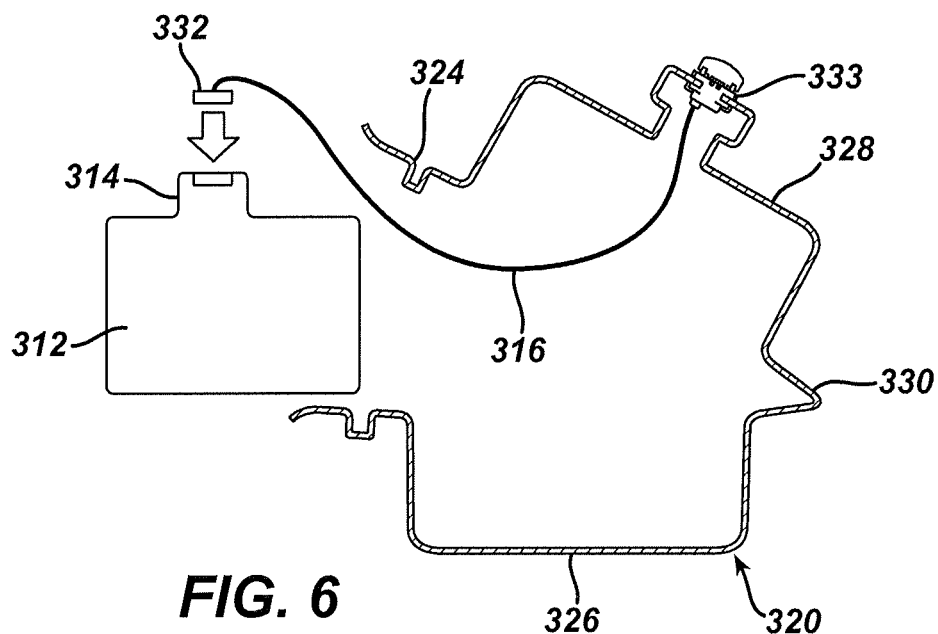
FIG. 6 depicts a side, cross sectional view of the compartment of FIG. 5.
Figure 7:
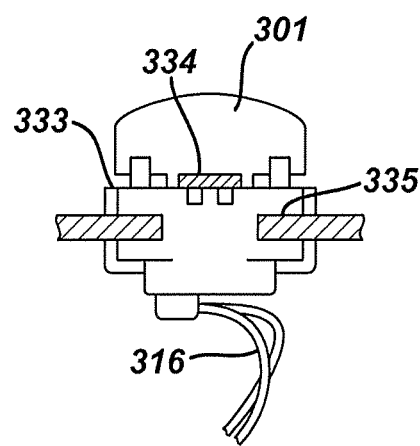
FIG. 7 depicts a side, partially cross-sectional view of the electrical contacts of the compartment of FIG. 5.

As shown in FIG. 5-7, other exemplary versions and ways of delivering power to a medical device (300) involve using a clamshell compartment (320). Compartment (320) may be attached to a handle portion (302) of medical device (300). Compartment (320) may be selectively attached to handle portion (302) via a twist lock mechanism, a snap lock mechanism, or any other suitable mechanism as would apparent to one of ordinary skill in the art in view of the teachings herein. For example, compartment (320) may be readily incorporated into any of the devices shown in U.S. Pat. No. 6,500,176, U.S. Pat. No. 7,416,101, U.S. Pat. No. 7,738,971, U.S. Pub. No. 2009/0209990 (now U.S. Pat. No. 8,657,174), U.S. Pub. No. 2006/0079874 (now abandoned), U.S. Pub. No. 2007/0191713 (now abandoned), U.S. Pub. No. 2007/0282333 (now abandoned), or U.S. Pub. No. 2008/0200940 (now abandoned). Alternatively, any of the devices shown in U.S. Pat. No. 6,500,176, U.S. Pat. No. 7,416,101, U.S. Pat. No. 7,738,971, U.S. Pub. No. 2009/0209990 (now U.S. Pat. No. 8,657,174), U.S. Pub. No. 2006/0079874 (now abandoned), U.S. Pub. No. 2007/0191713 (now abandoned), U.S. Pub. No. 2007/0282333 (now abandoned), or U.S. Pub. No. 2008/0200940 (now abandoned) may be adapted to incorporate compartment (320) into the device such that compartment (320) forms an integral component of the device. Compartment (320) of the present example holds a battery (312), though it should be understood that compartment (320) may hold various other components, electrical and/or otherwise, in addition to or in lieu of holding battery (312). It will also be appreciated that compartment (320) allows use of a non-sterile battery (312) to power medical device (300), without compromising the sterility of medical device (300).

FIG. 6 shows a closer view of how compartment (320) will fit battery (312) in this example. Battery (312) has a rectangular shape, and accordingly, compartment (320) also has a rectangular shape. However, compartment (320) need not be rectangular. Compartment (320) may comprise any shape suitable to store battery (312) as would be apparent to one of ordinary skill in the art in view of the teachings herein. Compartment (320) has a clamshell-like configuration that is operable to enclose battery (312). In particular, compartment (320) comprises a base (326), a lid (328), and a living hinge (330) connecting base (326) and lid (328). However, compartment (320) need not be configured like a clamshell. For example, compartment (320) may comprise a separate lid (328) and base (326) that snaps together to enclose battery (312). Other suitable shapes and constructions for compartment (320) will be apparent to one of ordinary skill in the art in view of the teachings herein.

Compartment (320) further comprises a sealing member (324) encircling the rim of compartment (324). In the illustrated version, sealing member (324) provides a snap fit between lid (328) and base (326), but other sealing member (324) structures may be used as would be apparent to one of ordinary skill in the art in view of the teachings herein. Sealing member (324) provides a tight enough seal such that battery (312) may be placed into compartment (320), which is then shut, to prevent battery (312) from contaminating medical device (300) being used with compartment (320).

Battery (312) further comprises a terminal post (314) at the top of battery (312). Terminal post (314) of battery (312) may be connected to a first contact (332). First contact (332) electrically couples with terminal post (314) when a user attaches first contact (332) to terminal post (314), such as by snap fitting. Compartment (320) further comprises a second contact (333) and a cable (316) connecting first contact (332) and second contact (333). Cable (316) comprises, for example, a coated wire or any other suitable conductive means to establish electrical coupling between first contact (332) and second contact (333) as would be apparent to one of ordinary skill in the art in view of the teachings herein. Thus, when battery (312) is attached to first contact (332), battery (312) is in electrical communication with second contact (333) as well via cable (316). In some alternative versions, rather than using cable (316) to establish electrical communication between first contact (332) and second contact (333), compartment (320) may be shaped to hold battery (312) such that when compartment (320) is closed, first contact (332) and second contact (333) are aligned to establish electrical communication. It will further be appreciated that first contact (332) could be omitted in some versions such that terminal post (314) directly contacts second contact (333) upon closure of container. It will also be appreciated that terminal post (314) comprises a positive and negative terminal to connect to corresponding contacts on first contact (332). It will be appreciated that in some versions, the positive and negative terminals may be on opposite sides of battery (312), thus, a portion of first contact (332) may connect to one portion of battery (312) whereas another portion of first contact (332) may connect to another portion of battery (312).

As can be seen in FIG. 7, cable (316) connects to second contact (333). In the exemplary version, the wall of lid (328) extends into an annular recess (335) of second contact (333). Thus, it will be appreciated that by extending into annular recess (335), second contact (333) and lid (328) maintain a sterile barrier such that use of a non-sterile battery (312) in compartment (320 with a sterile medical device will not compromise the sterility of the medical device. Second contact (333) presents a device contact (334), which electrically communicates to communication portion (301), which may electrically communicate with a medical device to deliver electrical power to a medical device. Device contact (334) comprises a positive and negative terminal, but it will be appreciated that other configurations may be used as well. For example, any suitable number of terminals may be used as would be apparent to one of ordinary skill in the art in view of the teachings herein.

Thus, one exemplary method of using compartment (320) involves first opening compartment (320). Once compartment (320) is opened, a user may connect first contact (332) to terminal post (314) of battery (312). The user then places battery (312) into compartment (320) and shuts compartment (320). Sealing member (324) is used to ensure a seal for shut compartment (320). At this point, even though battery (312) may not be sterile, the outer surface of compartment (320) is sterile, therefore, compartment (320) may be connected to medical device (300) to deliver electrical power to medical device (300) without concern over whether battery (312) may compromise the sterility of medical device (300).

Figure 8A:
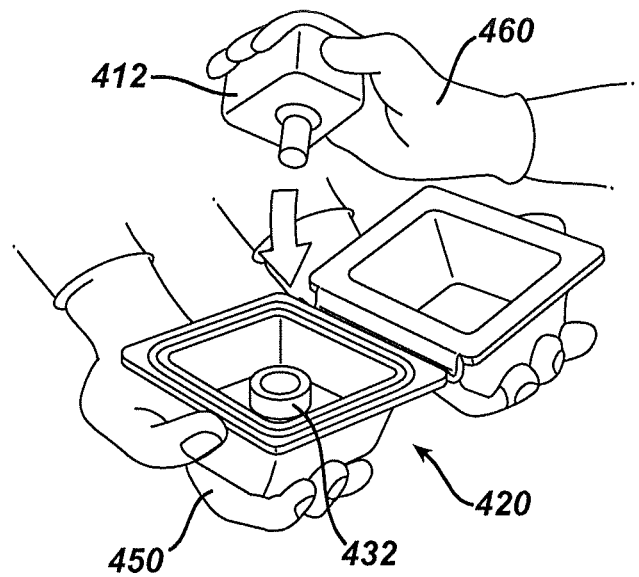
FIG. 8A depicts a perspective view of an alternative version of a compartment having a bulkhead connection, in an open configuration.
Figure 8B:
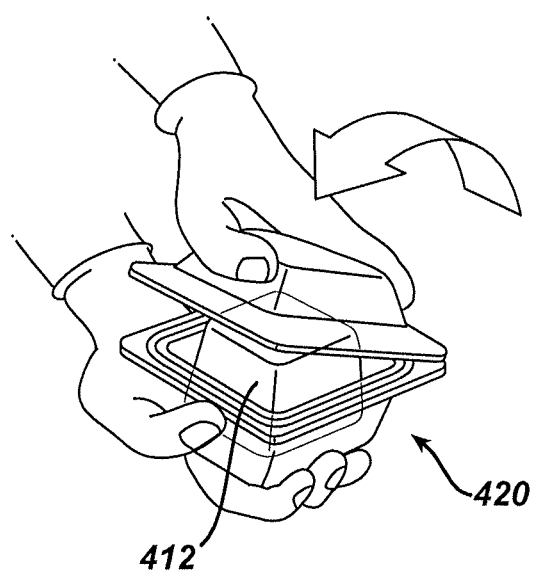
FIG. 8B depicts a perspective view of the compartment of FIG. 8A in a closed configuration.
Figure 9:
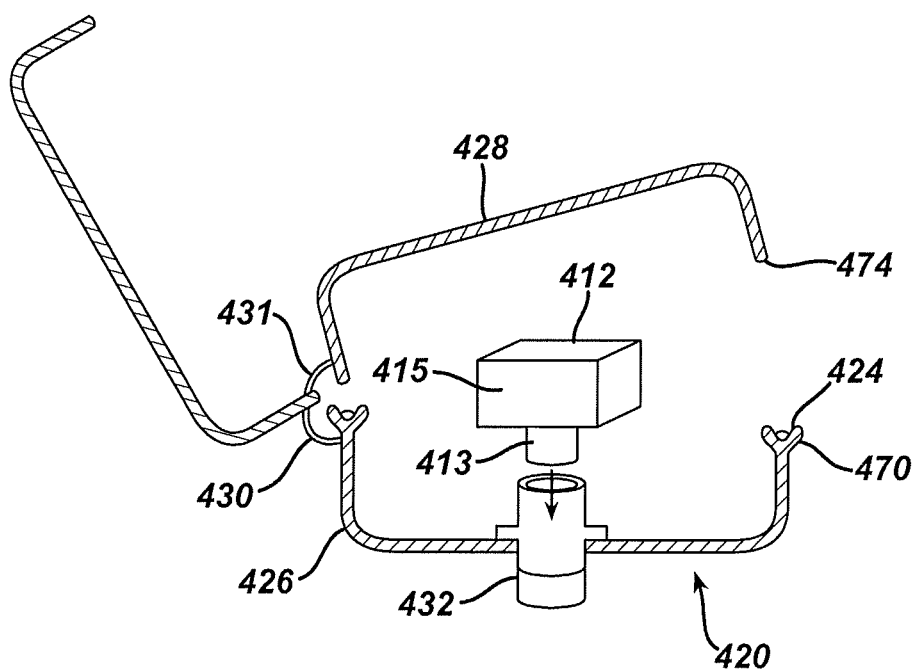
FIG. 9 depicts a side, cross sectional view of the compartment of FIG. 8A.

FIGS. 8-9 depict an alternative version of a clamshell compartment (420) having a bulkhead connection (432) for a battery (412). As can be seen in FIGS. 8A and 8B, battery (412) may be placed into compartment (420). Since the outer surface of compartment (420) is sterile in this example, a sterile set of hands (450) may be used to open compartment (420) in preparation for receiving battery (412) in compartment. A non-sterile set of hands (460) holds battery (412) prior to inserting battery (412) into compartment (420). The user with non-sterile set of hands (460) places battery (412) into compartment (420) such that battery (412) engages bulkhead connection (432). The user with sterile set of hands (450) may then close compartment (420) to seal non-sterile battery (412) in compartment (420). Then compartment (420) may be connected to or integrally formed with a medical device such as any of those shown in U.S. Pat. No. 6,500,176, U.S. Pat. No. 7,416,101, U.S. Pat. No. 7,738,971, U.S. Pub. No. 2009/0209990 (now U.S. Pat. No. 8,657,174), U.S. Pub. No. 2006/0079874 (now abandoned), U.S. Pub. No. 2007/0191713 (now abandoned), U.S. Pub. No. 2007/0282333 (now abandoned), or U.S. Pub. No. 2008/0200940 (now abandoned). Since the outer surface of compartment (420) is sterile, and because non-sterile battery (412) is sealed within compartment (420), the medical device can be used without non-sterile battery (412) being exposed to the medical device to compromise the sterility of the medical device.

FIG. 9 shows a closer view of compartment (420) having a lid (428) and a base (426) connected by a living hinge (430). In some alternative versions, lid (428) and base (426) may be separate components and connected with, for example, a tether (431) until lid (428) and base (426) are ready to mate. Lid (428) comprises a lid edge (474) and base (426) comprises a base edge (470) where lid edge (474) and base edge (470) selectively meet at a sealing portion (424), which will be described in further detail below.

Battery (412) of the present example comprises a cylindrical projection (413) to engage bulkhead connection (432). Bulkhead connection (432) also comprises a generally cylindrical shape in this example, though it should be understood that any other suitable shapes may be used as would be apparent to one of ordinary skill in the art in view of the teachings herein. Body (415) of battery (412) is larger than projection (413) such that when battery (412) is connected to bulkhead connection (432), bulkhead connection (432) abuts body (415) and furthermore provides structural support for battery (412). Bulkhead connection (432) also serves to stabilize battery (412) within compartment (420) such that battery (412) does not rattle within compartment (420).

In addition, bulkhead connection (432) provides a physical and electrical coupling between battery (412) and a medical device, for example, such as any of the devices shown in U.S. Pat. No. 6,500,176, U.S. Pat. No. 7,416,101, U.S. Pat. No. 7,738,971, U.S. Pub. No. 2009/0209990 (now U.S. Pat. No. 8,657,174), U.S. Pub. No. 2006/0079874 (now abandoned), U.S. Pub. No. 2007/0191713 (now abandoned), U.S. Pub. No. 2007/0282333 (now abandoned), or U.S. Pub. No. 2008/0200940 (now abandoned). As bulkhead connection (432) provides electrical coupling between battery (412) and a medical device, it will be appreciated that a pair of contacts within bulkhead connection (432) provide a conductive pass through that allows communication of power from battery (412) through bulkhead connection (432) to the medical device. It should therefore be understood that bulkhead connection (432) can connect to a medical device to power the medical device when battery (412) is inserted into bulkhead connection (432).

Figure 10A:
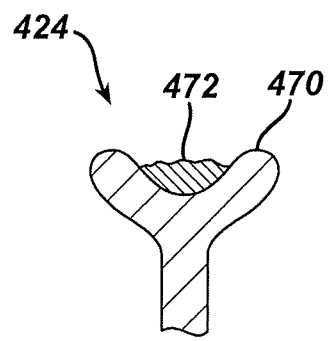
FIG. 10A depicts a partial side, cross-sectional view of the sealing member of the compartment of FIG. 7.
Figure 10B:
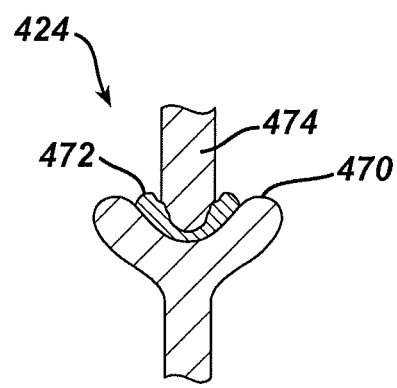
FIG. 10B depicts a partial side, cross-sectional view of the sealing member shown in FIG. 10A with the lid of the compartment closed upon the sealing member.

To ensure a proper seal to protect the sterile medical device from battery (412), which may be non-sterile, sealing portion (424) is used to seal compartment (420) once compartment (420) is closed. FIGS. 10A and 10B show sealing portion (424) defined by mating lid edge (474) and base edge (470). Base edge (470) near sealing portion (424) has a shallow bowl-like shape, which holds a sealing material (472). Sealing material (472) may comprise a deformable adhesive which may comprise a gum or a foam material. Sealing material (472) may further comprise an elastomer. Other suitable sealing material (472) may be used as would be apparent to one of ordinary skill in the art in view of the teachings herein.

As lid edge (474) mates with base edge (470), lid edge (474) presses against sealing material (472) as shown in FIG. 10B. As lid edge (474) presses against sealing material (472), sealing material (472) deforms to ensure that lid edge (474) and base edge (470) form an effective seal. Furthermore, in the exemplary version, sealing material (472) provides a substantially secure fitting between lid edge (474) and base edge (470), thereby enabling lid (428) to stay closed with a hermetic seal. In particular, sealing material (472) adheres lid edge (474) and base edge (470) together to prevent compartment (420) from inadvertently opening in the present example. In some other versions, rather than using an adhesive, a latching mechanism or a snap fit mechanism could be used, or any other suitable closing mechanism could be used as would be apparent to one of ordinary skill in the art. A separate sealing material (472) and/or other sealing components (e.g., gaskets, etc.) may be used with such a closing mechanism. With compartment (420) closed and sealed, compartment (420) may be attached through bulkhead connection (432) to a medical device such as those shown in U.S. Pat. No. 6,500,176, U.S. Pat. No. 7,416,101, U.S. Pat. No. 7,738,971, U.S. Pub. No. 2009/0209990 (now U.S. Pat. No. 8,657,174), U.S. Pub. No. 2006/0079874 (now abandoned), U.S. Pub. No. 2007/0191713 (now abandoned), U.S. Pub. No. 2007/0282333 (now abandoned), or U.S. Pub. No. 2008/0200940 (now abandoned). Also, it will be appreciated that any of the devices shown in U.S. Pat. No. 6,500,176, U.S. Pat. No. 7,416,101, U.S. Pat. No. 7,738,971, U.S. Pub. No. 2009/0209990 (now U.S. Pat. No. 8,547,174), U.S. Pub. No. 2006/0079874 (now abandoned), U.S. Pub. No. 2007/0191713 (now abandoned), U.S. Pub. No. 2007/0282333 (now abandoned), or U.S. Pub. No. 2008/0200940 (now abandoned ) could be adapted to integrate compartment (420) into the device for use in delivering electrical power to the device.

V. Electrical Feedthrough

Figure 11:
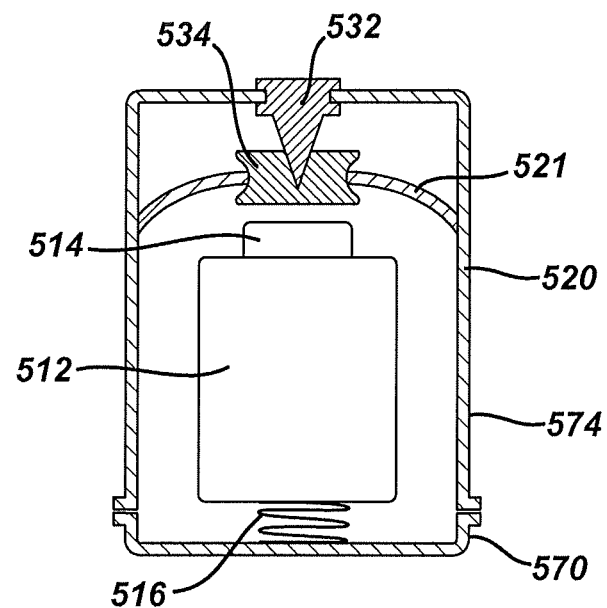
FIG. 11 depicts a side view of an exemplary alternative compartment having a spring in the base of the compartment.

FIG. 11 shows an exemplary version of a compartment (520) to establish an electrical feedthrough from a battery (512) to a medical device. For example, such an electrical feedthrough could be used with or adapted for use with any of the devices shown in U.S. Pat. No. 6,500,176, U.S. Pat. No. 7,416,101, U.S. Pat. No. 7,738,971, U.S. Pub. No. 2009/0209990 (now U.S. Pat. No. 8,657,174), U.S. Pub. No. 2006/0079874 (now abandoned), U.S. Pub. No. 2007/0191713 (now abandoned), U.S. Pub. No. 2007/0282333 (now abandoned), or U.S. Pub. No. 2008/0200940 (now abandoned). It will be appreciated that compartment (520) may be used to hold battery (512), which in some cases may not be sterile. Compartment (520) of the present example may be sealed such that battery (512) may be used to locally deliver electrical power to a sterile medical device such as any of the devices shown in U.S. Pat. No. 6,500,176, U.S. Pat. No. 7,416,101, U.S. Pat. No. 7,738,971, U.S. Pub. No. 2009/0209990 (now U.S. Pat. No. 8,657,174), U.S. Pub. No. 2006/0079874 (now abandoned), U.S. Pub. No. 2007/0191713 (now abandoned), U.S. Pub. No. 2007/0282333 (now abandoned), or U.S. Pub. No. 2008/0200940 (now abandoned) without compromising the sterility of the device despite being in electrical communication with the non-sterile battery (512). Various suitable ways in which compartment (520) may be integrated into medical device will be apparent to one of ordinary skill in the art in view of the teachings herein.

Compartment (520) of the present example is defined by a housing (574). In some versions, housing (574) is recessed within a medical device, such as any of those listed above. Housing (574) includes a spike electrode (532), a septum (534), and a web (521). Spike electrode (532) projects inwardly into the interior defined by housing (574), and is positioned within septum (534). As shown in FIG. 11, web (521) is resiliently biased to keep the tip of spike electrode (532) within septum (534) until septum (534) is engaged by a battery (512) as described below. As another merely illustrative example, web (521) may be resiliently biased to keep septum (534) spaced away from spike electrode (532) until septum (534) is engaged by battery (512).

Housing (574) is sized and configured to receive battery (512). In particular, a battery (512) may be placed in compartment (520), and a cap (570) may then be secured to housing (574) to secure battery (512) within compartment (520). A spring (516) secured to cap (570) is resiliently biased to urge battery (512) toward septum (534) when cap (570) is secured to housing (574). As battery (512) pushes against septum (534), web (521) deforms such that spike electrode (532) penetrates septum (534) to electrically couple with a terminal post (514) of battery (512) to electrically couple battery (512) with a medical device. In other words, upon contact with terminal post (514), battery (512) delivers power to the medical device through spike electrode (532). In some other alternative versions, compartment (520) may be embedded in a medical device.

Web (521) and septum (534) together form a fluid tight seal such that battery (512) sits in a fluid tight compartment (520). Septum (534) is further configured to maintain the fluid tight seal even when septum (534) is pierced by spike electrode (532).

While the exemplary version comprises a single spike electrode (532), it will be appreciated that any other suitable number of spike electrodes (532) may be used as would be apparent to one of ordinary skill in the art in view of the teachings herein. It should also be understood that spring (516) may be initially recoiled and, upon direction or triggering by the user, be extended to selectively urge battery (512) toward septum (534).

When the user is ready to locally power the medical device for use, battery (512) may be placed into compartment (520) such that terminal post (514) abuts septum (534). Then, a user with sterilized hands may place cap (570) over battery (512) to hermetically seal battery (512) in compartment (520). Thereafter, it will be appreciated that spring (516) will gently urge battery (512) against septum (534). Web (521) will accordingly deform to allow spike electrode (532) to further penetrate septum (534) until spike electrode (534) comes into contact with terminal post (514) of battery (512). As a result, electrical power may then be delivered to the medical device.

Figure 12:
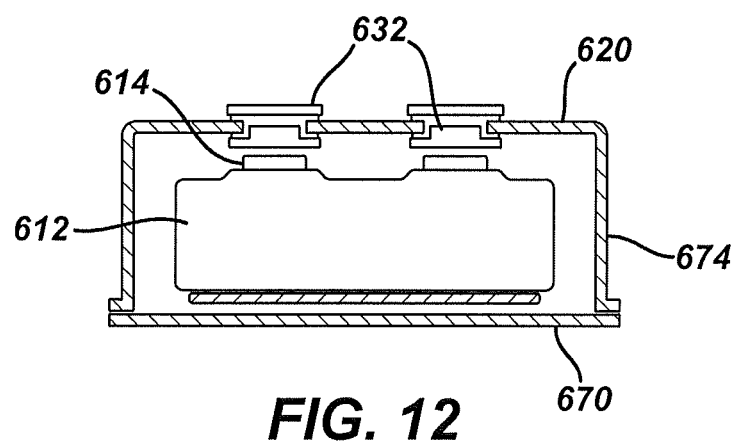
FIG. 12 depicts a side view of an alternative connection device having dual feedthrough contacts.

FIG. 12 shows another alternative version of a compartment (620) to deliver power from a battery (612) to, for example, a medical device, such as any of the medical devices described in any of the references cited herein. Compartment (620) holds battery (612) as shown by a cap (670) and a housing (674), which seal battery (612) in compartment (620). Also embedded into compartment (620) are two feedthrough contacts (632) which extend from outside of compartment (620) to the inside of compartment (620) to contact terminal posts (614) of battery (612). Feedthrough contacts (632) are held in place within the wall of compartment (620) with for example, an adhesive seal, film, gel, overmolding, using elastomer seals, plastic welding or any other suitable sealing material as would be apparent to one of ordinary skill in the art in view of the teachings herein. In the exemplary version, an annular recess formed in feedthrough contacts (632) further secure the wall or compartment (620) to form a fluid tight seal such that non-sterile components within compartment (620) do not contaminate sterile components such as a medical device, for example, any of those shown in U.S. Pat. No. 6,500,176, U.S. Pat. No. 7,416,101, U.S. Pat. No. 7,738,971, U.S. Pub. No. 2009/0209990 (now U.S. Pat. No. 8,657,174), U.S. Pub. No. 2006/0079874 (now abandoned), U.S. Pub. No. 2007/0191713 (now abandoned), U.S. Pub. No. 2007/0282333 (now abandoned), or U.S. Pub. No. 2008/0200940 (now abandoned). Terminal posts (614) of battery (612) are in electrical communication with feedthrough contacts (632) thereby allowing compartment (620) to deliver power to, for example, a medical device by electrically coupling with feedthrough contacts (632).

In some other versions, rather than two feedthrough contacts (632), a single feedthrough contact (not shown) may be used instead. A seal between compartment (620) and a single feedthrough contact may be achieved by, for example, overmolding, using elastomer seals, or plastic welding. Other sealing methods may be used as would be apparent to one of ordinary skill in the art in view of the teachings herein. Furthermore, in some versions, feedthrough contacts (632) may not be used at all. Rather, an electroconductive polymer may be embedded into the wall of compartment (620), which can serve as a conductive feedthrough between battery (612) and the exterior of compartment (620).

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Embodiments of the present invention have application in conventional endoscopic and open surgical instrumentation as well as application in robotic-assisted surgery.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An apparatus comprising:
    (a) a battery pack;
    (b) a connection feature in communication with the battery pack, wherein the connection feature comprises at least one electrode operable to deliver power from the battery pack to another device;
    (c) a protective layer, wherein the protective layer covers at least a portion of the battery pack, wherein the protective layer further covers at least a portion of the connection feature such that the protective layer forms a fluid tight seal around the connection feature;
    (d) a penetrating feature, wherein the penetrating feature has sufficient sharpness to penetrate the protective layer, wherein the penetrating feature is formed of an electrically conductive material; and
    (e) a protective feature having sufficient structural stability to selectively maintain a position of the penetrating feature or the protective layer relative to the other to thereby maintain a gap between the penetrating feature and the protective layer.

2. The apparatus of claim 1, wherein the penetrating feature is integral with the at least one electrode.

3. The apparatus of claim 1, wherein the penetrating feature has a conical shape.

4. The apparatus of claim 1, wherein the protective layer comprises an elastic film material.

5. The apparatus of claim 1, wherein the at least one electrode comprises a pair of electrodes, wherein the protective layer surrounds both of the electrodes.

6. The apparatus of claim 1, further comprising a conduction foam positioned between the at least one electrode and the penetrating feature, wherein the conduction foam is operable to provide electrical communication between the at least one electrode and the electrically powered medical device.

7. The apparatus of claim 6, wherein conduction foam in enclosed by a sterile barrier and is in contact with an exposed contact feature, wherein the exposed contact feature is configured to provide electrical communication between the conduction foam and the medical device.

8. The apparatus of claim 1, wherein the protective layer comprises a thinned pierce-able region.

9. The apparatus of claim 1, further comprising a spring in communication with the battery pack, wherein the spring is resiliently biased to urge the battery toward the connection feature.

10. The apparatus of claim 1, wherein the protective feature comprises a web supporting the penetrating feature, wherein the web is resiliently biased to urge the penetrating feature away from the protective layer.

11. The apparatus of claim 1, wherein the battery pack comprises at least one lithium ion battery.

12. The apparatus of claim 1, wherein the protective layer comprises a septum, wherein the penetrating feature is operable to penetrate the septum to provide power to the medical device.

13. The apparatus of claim 1, wherein the electrically powered medical device presents an inverted cone-shaped recess configured to receive the penetrating feature.

14. The apparatus of claim 1, wherein the protective feature comprises a stand-off feature of the battery pack configured to space the protective layer away from the penetrating feature.

15. An apparatus comprising:
    (a) an electrically powered medical device, wherein the medical device includes a connection feature;
    (b) a compartment selectively attachable and detachable with the electrically powered medical device, wherein an internal portion of the compartment is operable to receive at least one battery;
    (c) a connection feature extending through a wall of the compartment, wherein the compartment forms a seal about a perimeter of the connection feature, wherein the connection feature is formed of an electrically conductive material
    wherein the connection feature of the medical device is structured to selectively couple with the connection feature of the compartment.

16. The apparatus of claim 15, wherein the connection feature comprises a bulkhead connection.

17. A method for providing power to an electrically powered, medical device by using a battery pack and a membrane barrier, wherein the battery pack comprises at least one battery contained therein, wherein the battery pack further comprises at least one electrode, the method comprising:
    (a) maintaining a gap between the membrane barrier and the at least one electrode via a web member;
    (b) positioning the battery pack proximate to the medical device such that the web member and the membrane barrier are positioned between the battery pack and the medical device, wherein the membrane barrier isolates the battery pack from the medical device such that the medical device is substantially isolated from contamination by the battery pack;
    (c) collapsing the web member toward the membrane barrier by pressing the medical device against the exterior of the web member thereby eliminating the gap between the membrane barrier and the at least one electrode and thereby breaching the membrane barrier between the battery pack and the medical device, wherein the act of breaching the membrane barrier comprises urging the at least one electrode against the membrane barrier; and
    (d) establishing electrical communication between the at least one battery and the medical device through the at least one electrode after or upon breaching the membrane barrier.

18. The method of claim 17, wherein the act of breaching the membrane barrier comprises piercing the membrane barrier with the at least one electrode.

19. The method of claim 17, wherein the membrane barrier comprises an elastic membrane barrier operable to maintain a fluid tight seal.

\* \* \* \* \*